US011052356B2

(12) United States Patent
Ansley et al.

(10) Patent No.: US 11,052,356 B2
(45) Date of Patent: Jul. 6, 2021

(54) AIR TREATMENT APPLIANCE

(71) Applicant: Prolitec Inc., Milwaukee, WI (US)

(72) Inventors: Matthew Ansley, Muskego, WI (US); Nathan Sward, Milwaukee, WI (US); Andrew Williams, Elm Grove, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 16/116,711

(22) Filed: Aug. 29, 2018

(65) Prior Publication Data

US 2019/0105615 A1 Apr. 11, 2019

Related U.S. Application Data

(63) Continuation of application No. 15/659,527, filed on Jul. 25, 2017, now Pat. No. 10,086,340.

(60) Provisional application No. 62/366,987, filed on Jul. 26, 2016.

(51) Int. Cl.
| | |
|---|---|
| *B01F 3/00* | (2006.01) |
| *B01F 3/04* | (2006.01) |
| *B05B 7/00* | (2006.01) |
| *B05B 7/24* | (2006.01) |

(Continued)

(52) U.S. Cl.
CPC ............ *B01F 3/04063* (2013.01); *A61L 9/14* (2013.01); *B05B 7/0012* (2013.01); *B05B 7/2424* (2013.01); *B05B 7/265* (2013.01); *A61L 2209/111* (2013.01); *A61L 2209/133* (2013.01); *B05B 7/24* (2013.01)

(58) Field of Classification Search
CPC .... B01F 3/04; B01F 3/04007; B01F 3/04085; B05B 17/0646; B05B 17/0684; B41J 2/1755; B41J 2/17523; B41J 2/17526; B41J 2/17553; B41J 2/14024; B41J 2/14072
USPC ....... 261/142, 94, 97, 99, DIG. 65, DIG. 88, 261/DIG. 89; 347/49, 50, 65, 85, 86
See application file for complete search history.

(56) References Cited

U.S. PATENT DOCUMENTS 2,635,921 A * 4/1953 Deutsch ................ B05B 7/2429 239/426
4,007,238 A * 2/1977 Glenn .................... A61M 11/06 261/78.2

(Continued)

FOREIGN PATENT DOCUMENTS

EP 2 433 656 A1 3/2012

*Primary Examiner* — Viet Le
(74) *Attorney, Agent, or Firm* — Seed IP Law Group LLP

(57) ABSTRACT

An air treatment system is provided which includes an appliance and a replaceable cartridge installable therein. The replaceable cartridge contains a liquid compound to be aerosolized and has a cartridge outlet through which the aerosolized compound is discharged during operation. A pump is provided to supply air to the replaceable cartridge to generate the aerosolized compound from the liquid compound contained in the replaceable cartridge, and a controller is provided for controlling the pump to supply the air to the replaceable cartridge to generate and discharge the aerosolized compound from the appliance. The appliance may further include a lift mechanism to assist in receiving the cartridge and moving the cartridge from a loading position to an operational position. The appliance may also communicate with a smartphone or other external device to provide additional functionality.

25 Claims, 10 Drawing Sheets

(51) Int. Cl.
*A61L 9/14* (2006.01)
*B05B 7/26* (2006.01)

(56) References Cited

U.S. PATENT DOCUMENTS

| | | | | |
|---|---|---|---|---|
| 4,190,046 A * | 2/1980 | Virag | ..................... | A61M 11/06 128/200.21 |
| 4,595,564 A * | 6/1986 | Spector | ................. | B05B 7/1686 219/433 |
| 5,223,182 A * | 6/1993 | Steiner | ................... | A61L 9/122 261/26 |
| 5,533,497 A * | 7/1996 | Ryder | .................. | B05B 7/2435 128/200.21 |
| 5,975,675 A * | 11/1999 | Kim | ........................ | B41J 3/407 347/20 |
| 6,170,937 B1 * | 1/2001 | Childers | .............. | B41J 2/16538 347/85 |
| 6,196,219 B1 * | 3/2001 | Hess | ................. | A61M 15/0085 128/200.21 |
| 6,261,347 B1 * | 7/2001 | Moreland | .............. | C09D 11/38 106/31.02 |
| 6,293,474 B1 * | 9/2001 | Helf | ...................... | A01M 1/205 239/102.1 |
| 6,323,912 B1 * | 11/2001 | McIntyre | ............. | H04N 1/2112 348/552 |
| 6,357,671 B1 * | 3/2002 | Cewers | ................ | B05B 12/081 239/102.1 |
| 6,371,451 B1 * | 4/2002 | Choi | ..................... | A45D 34/02 261/115 |
| 6,405,944 B1 * | 6/2002 | Benalikhoudja | ........ | A61L 9/145 128/200.18 |
| 6,802,460 B2 * | 10/2004 | Hess | ......................... | A61L 2/18 239/102.1 |
| 6,950,607 B2 * | 9/2005 | Yip | ........................ | A61L 9/035 392/390 |
| 6,968,124 B1 * | 11/2005 | Varanasi | ............. | A01M 1/2077 392/392 |
| 7,070,121 B2 * | 7/2006 | Schramm | .............. | A01M 1/205 239/102.1 |
| 7,152,758 B2 * | 12/2006 | Fazzio | ................... | A45D 34/02 222/145.1 |
| 7,281,811 B2 * | 10/2007 | Thuot Rann | ............ | A61L 9/037 219/220 |
| 7,367,661 B2 * | 5/2008 | Hess | ................... | B05B 17/0638 239/102.1 |
| 7,387,265 B2 * | 6/2008 | Hess | ....................... | A61L 9/145 239/102.1 |
| 7,389,943 B2 * | 6/2008 | Jaworski | ............... | A01M 1/205 239/102.2 |
| 7,469,844 B2 * | 12/2008 | Conway | ............. | B05B 17/0607 239/102.2 |
| 7,581,718 B1 * | 9/2009 | Chang | ................... | A61M 11/06 261/78.2 |
| 7,712,683 B2 * | 5/2010 | Robert | ..................... | A61L 9/14 239/338 |
| 7,734,159 B2 * | 6/2010 | Beland | .................... | A61L 9/035 392/390 |
| 7,878,418 B2 * | 2/2011 | Sevy | ..................... | A61M 11/06 128/200.18 |
| 7,930,068 B2 * | 4/2011 | Robert | .................... | A61L 9/14 700/283 |
| 8,006,698 B2 * | 8/2011 | Boehm | .................. | A61M 11/02 128/207.18 |
| 8,006,918 B2 * | 8/2011 | Mahoney, III | ........ | H01L 41/042 239/102.1 |
| 8,020,573 B2 * | 9/2011 | Lamers | .................... | A61L 9/14 137/12 |
| 8,170,405 B2 * | 5/2012 | Harris | ................... | A01M 1/2033 392/386 |
| 8,251,500 B2 * | 8/2012 | Yamada | .................. | B41J 2/185 347/86 |
| 8,336,543 B2 * | 12/2012 | Holmquist-Brown | ...................... | A62B 18/088 128/202.22 |
| 8,342,664 B2 * | 1/2013 | Wang | .................... | B41J 2/17513 347/7 |
| 8,584,967 B2 * | 11/2013 | Feriani | ................ | B05B 17/0638 239/102.1 |
| 8,596,264 B2 * | 12/2013 | Sommer | ................ | A61M 11/06 128/200.14 |
| 8,625,977 B2 * | 1/2014 | Cheung | .................... | A61L 9/037 392/386 |
| 8,708,470 B1 * | 4/2014 | Blowfield | ............ | B41J 2/17523 347/86 |
| 8,851,644 B2 * | 10/2014 | Shirono | ............... | B41J 2/17506 347/84 |
| 8,855,827 B2 * | 10/2014 | Weening | .................. | A61L 9/14 239/11 |
| 8,876,086 B2 * | 11/2014 | Burke | ..................... | A61L 9/122 261/107 |
| 9,015,989 B1 * | 4/2015 | Zeamer | .................. | A01M 1/2005 239/37 |
| 9,033,553 B2 * | 5/2015 | Li | ........................... | F21S 10/04 362/311.01 |
| 9,067,425 B2 * | 6/2015 | Blowfield | ............ | B41J 2/17526 |
| D735,309 S * | 7/2015 | Sevy | ...................... | A61L 2/00 D23/364 |
| 9,162,004 B1 * | 10/2015 | Ansley | ................ | B01F 15/0244 |
| 9,168,756 B2 * | 10/2015 | Harada | .................. | B41J 2/1721 |
| 9,211,980 B1 * | 12/2015 | Gruenbacher | ............ | A61L 9/14 |
| 9,248,461 B2 * | 2/2016 | Ansley | ................ | B01F 3/0446 |
| 9,278,365 B2 * | 3/2016 | Banco | ..................... | A61L 9/046 |
| 9,333,523 B2 * | 5/2016 | Lowy | .................... | B05B 15/58 |
| 9,352,063 B2 * | 5/2016 | Ooten | .................... | A61L 9/127 |
| 9,358,562 B2 * | 6/2016 | Ansley | ..................... | A61L 9/145 |
| 9,480,767 B1 * | 11/2016 | Ansley | ...................... | A61L 9/14 |
| 9,480,769 B2 * | 11/2016 | Sevy | ........................ | A61L 9/14 |
| 9,486,552 B1 * | 11/2016 | Ansley | ..................... | A61L 9/14 |
| 9,585,982 B1 * | 3/2017 | Hafer | ..................... | A61L 9/125 |
| 9,745,976 B2 * | 8/2017 | Ansley | ................ | B01F 3/0446 |
| 9,797,396 B2 * | 10/2017 | Ansley | ................ | B01F 3/04007 |
| 2002/0114744 A1 * | 8/2002 | Chiao | .................... | A61L 9/014 422/124 |
| 2002/0130146 A1 | 9/2002 | Borut et al. | | |
| 2002/0192255 A1 * | 12/2002 | Schiavo | ................... | A01M 1/2077 424/405 |
| 2003/0206834 A1 * | 11/2003 | Chiao | ..................... | A61L 9/014 422/124 |
| 2003/0218077 A1 * | 11/2003 | Boticki | ............... | B05B 17/0646 239/102.1 |
| 2004/0032468 A1 * | 2/2004 | Killmeier | ................ | B41J 2/1753 347/85 |
| 2004/0235430 A1 * | 11/2004 | Ma | ........................... | A61L 9/03 455/90.1 |
| 2005/0220664 A1 | 10/2005 | Hitzler et al. | | |
| 2006/0065755 A1 * | 3/2006 | Sugita | ............... | A61M 15/0065 239/1 |
| 2006/0219814 A1 * | 10/2006 | Benalikhoudja | ...... | B05B 7/0869 239/340 |
| 2007/0020033 A1 * | 1/2007 | Walsh | .................... | B43K 5/005 401/195 |
| 2007/0138326 A1 * | 6/2007 | Hu | ....................... | A01M 1/2038 239/690 |
| 2008/0164339 A1 * | 7/2008 | Duru | .................. | B05B 17/0646 239/102.2 |
| 2010/0154790 A1 * | 6/2010 | Merassi | ................... | B05B 1/14 128/200.18 |
| 2011/0290241 A1 * | 12/2011 | Maeda | .................. | A61M 11/005 128/200.14 |
| 2012/0018529 A1 * | 1/2012 | Gammon | ................. | A61L 9/03 239/6 |
| 2012/0205462 A1 | 8/2012 | Burke et al. | | |
| 2013/0334336 A1 * | 12/2013 | Haran | .................... | A61L 9/14 239/4 |
| 2014/0078229 A1 * | 3/2014 | Jackson | ................. | A61L 9/14 347/95 |
| 2014/0079597 A1 | 3/2014 | Segura Rius et al. | | |
| 2014/0212334 A1 | 7/2014 | Klein et al. | | |

(56) References Cited

U.S. PATENT DOCUMENTS

| | | | |
|---|---|---|---|
| 2015/0019029 A1 | 1/2015 | Chandler et al. | |
| 2015/0076716 A1* | 3/2015 | Roemburg | B05B 17/0653 |
| | | | 261/78.2 |
| 2015/0297776 A1 | 10/2015 | Conroy et al. | |
| 2015/0367013 A1* | 12/2015 | Gruenbacher | A61L 9/037 |
| | | | 239/13 |
| 2015/0367014 A1* | 12/2015 | Gruenbacher | B41J 2/0458 |
| | | | 392/387 |
| 2015/0367016 A1* | 12/2015 | Gruenbacher | A45D 34/00 |
| | | | 96/222 |
| 2015/0367356 A1* | 12/2015 | Gruenbacher | B41J 2/17513 |
| | | | 239/135 |
| 2015/0368001 A1* | 12/2015 | Gruenbacher | A61L 9/14 |
| | | | 222/52 |
| 2018/0028985 A1* | 2/2018 | Ansley | B05B 7/0012 |

* cited by examiner

FIG. 8A

- aera 10:34 AM
- Your Aera is currently offline. Please make sure your device is plugged in and connected to wifi
- ZEPHYR
- DEVICE IS OFF
- +
- −
- 100% Fragrance Remaining

FIG. 8B

- aera 10:34 AM
- NO NAME SET
- FRAGRANCE SCHEDULE
- 9:56a-10:56p  INTENSITY: 10
  MON TUE WED
- 9:57a-10:57a  INTENSITY: 3
  MON TUE
- ADD

FIG. 8C

- My Aera 10:34 AM
- DEVICES
- NO NAME SET
  Zephyr
- NO NAME SET
  Curiosity
- B16...
- NO NAME SET
- NO NAME SET
- ADD NEW DEVICE
- MY DEVICES   MY FRAGRAN

AIR TREATMENT APPLIANCE

CROSS-REFERENCE TO RELATED APPLICATIONS

This application is a continuation of U.S. patent application Ser. No. 15/659,527, filed Jul. 25, 2017, which claims benefit to U.S. Provisional Patent Application No. 62/366,987, filed Jul. 26, 2016, the entire contents of which are hereby incorporated by reference in their entireties.

BACKGROUND

Technical Field

The present disclosure relates generally to air treatment appliances and, more specifically, to air treatment appliances including a replaceable cartridge containing a liquid compound to be diffused or aerosolized and released into a space to be treated.

Description of the Related Art

Air treatment appliances in the past have had the ability to dispense scent compounds or other compounds throughout the atmosphere of desired spaces but can suffer from various drawbacks or deficiencies. For example, some air treatment appliances and replaceable cartridges thereof may be overly complex, costly and/or suffer from other deficiencies or drawbacks, such as, for example, discharging diffused or aerosolized matter with less than ideal characteristics, or the cartridges being susceptible to leakage, tampering, fouling and/or contamination.

BRIEF SUMMARY

The air treatment appliances and replaceable cartridges and other components thereof and related methods shown and described herein provide form factors that are robust, efficient, and particularly effective at treating spaces with a diffused or aerosolized compound from a liquid source.

At least one embodiment of a replaceable cartridge for a liquid diffusion device may be summarized as including: a cartridge housing including a plurality of housing pieces fixedly coupled together and defining an internal housing cavity partially filled with a liquid to be aerosolized; and a venturi device positioned within the internal housing cavity for generating aerosolized matter from the liquid contained in the internal housing cavity, wherein the plurality of housing pieces include an internal housing body defining at least a portion of a receptacle for the liquid to be aerosolized, an upper housing cap including an outlet through which the aerosolized matter is discharged during use, and an outer casing surrounding at least a lower portion of the internal housing body.

The internal housing body may be transparent or semi-transparent, the outer casing may be opaque, and the outer casing may include a window through which a level of the liquid to be aerosolized is viewable through an exposed portion of the internal housing body. The window of the outer casing may have a size and a shape sufficient to observe the liquid in the internal housing body as the liquid transitions between a full level and an empty level. The internal housing body may define at least a portion of a gas supply conduit that extends from a bottom end of the removable cartridge to the venturi device and through the liquid to be aerosolized. A liquid retention device may be positioned within the gas supply conduit adjacent the venturi device to retain liquid that may pass downward through the venturi device into the gas supply conduit. The internal housing body and the outer casing may each have a substantially cylindrical shape concentrically aligned. The replaceable cartridge may further include: an insert positioned above of the venturi device, the insert including an inlet to receive aerosolized matter generated by the venturi device, an outlet zone from which to discharge the aerosolized matter toward an external environment, and a tortuous passage extending between the inlet and the outlet zone; and a gasket positioned between an upper end of the insert and the upper housing cap, the gasket forming a cover over the tortuous passage extending between the inlet and the outlet zone of the insert. A first coupling arrangement may be provided to secure the upper housing cap to the internal housing body and a second coupling arrangement may be provided to secure the outer casing to the internal housing body. The first coupling arrangement may be configured to prevent non-destructive disassembly of the internal housing body from the upper housing cap, and the second coupling arrangement may be configured to enable disassembly of the outer casing from the internal housing body upon overcoming a threshold resistive force. The first coupling arrangement may include a coupling protrusion engaged with a coupling cavity, the coupling protrusion provided on one of an outer surface of the internal housing body and an inner surface of the upper housing cap, and the coupling cavity provided on the other one of the outer surface of the internal housing body and the inner surface of the upper housing cap, and the second coupling arrangement may include a second coupling protrusion engaged with a second coupling cavity, the second coupling protrusion provided on one of an outer surface of the internal housing body and an inner surface of the outer casing, and the second coupling cavity provided on the other one of the outer surface of the internal housing body and the inner surface of the outer casing.

At least one embodiment of a replaceable cartridge for a liquid diffusion device may be summarized as including: a cartridge housing defining an internal housing cavity partially filled with a liquid to be aerosolized; a venturi device positioned within the internal housing cavity for generating aerosolized matter from the liquid contained in the internal housing cavity; and an integrated circuit coupled to the cartridge housing having memory to store cartridge data associated with the replaceable cartridge.

The replaceable cartridge may further include an electrical interface in electrical communication with the integrated circuit to enable retrieval of the cartridge data by an external system contacting the electrical interface. The integrated circuit may be configured to enable contactless retrieval of the cartridge data. The cartridge housing may include a plurality of housing pieces fixedly coupled together, the plurality of housing pieces including: an internal body defining the internal housing cavity partially filled with the liquid to be aerosolized; a cap fixedly coupled to the internal body to enclose the diffusion head within a combination of the cap and the internal body; and an outer casing surrounding at least a lower portion of the internal body. The replaceable cartridge may further include a circuit board coupled to the cartridge housing, the circuit board comprising the integrated circuit and an electrical interface in electrical communication with the integrated circuit to enable retrieval of the cartridge data by an external system contacting the electrical interface. The circuit board may be located at a bottom end of the cartridge housing and may have an annular shape. The electrical interface may include at least one contact surface to mechanically couple the electrical interface with at least one circuit contact surface on the integrated circuit. The cartridge data may include cartridge identification data, liquid characteristic data, liquid level data and/or cartridge use data.

At least one embodiment of a liquid diffusion appliance configured to receive a replaceable cartridge and generate aerosolized matter from liquid contained within the replaceable cartridge may be summarized as including: an appliance housing including a cartridge port through which to receive the replaceable cartridge; and a lift mechanism provided within the appliance housing for moving the replaceable cartridge at least between a cartridge loading position and an operational positon.

The appliance housing may include one or more external housing pieces and one or more internal housing pieces coupled together to define a cartridge cavity extending into the appliance housing from the cartridge port. The lift mechanism may include: a lift carriage configured to move within the cartridge cavity; and an air stem provided on the lift carriage, the air stem being removably insertable in the replaceable cartridge for supplying air to the replaceable cartridge during use. The lift mechanism may further include a motor and a gearwheel driven by the motor, the gearwheel having a lift pin to interact with the lift carriage to raise and lower the lift carriage in correlation with rotation of the gearwheel by the motor. The lift carriage may include a lift cavity through which the lift pin extends, the lift cavity being sized and shaped to cause the lift pin to lose contact with the lift carriage as the lift carriage is moved to a weigh position. The liquid diffusion appliance may further include a force sensor positioned within the cartridge cavity to weigh the replaceable cartridge in the weigh position. The replaceable cartridge may include an integrated circuit coupled to the replaceable cartridge, the integrated circuit having at least one storage device to store cartridge data associated with the replaceable cartridge, and wherein the lift mechanism may include a lift carriage with electrical contacts arranged to interface with the electrical interface of the replaceable cartridge when the replaceable cartridge is installed in the liquid diffusion appliance for use. The lift mechanism may include a lift carriage for moving the replaceable cartridge between different positions, and the lift mechanism may be configured to prevent manual displacement of the lift carriage between the different positions.

At least one embodiment of an aerosol delivery system for discharging aerosolized matter may be summarized as including: a replaceable cartridge including an internal cavity partially filled with a liquid to be aerosolized and a venturi device positioned within the internal cavity for generating aerosolized matter from the liquid contained in the internal cavity; and an appliance configured to receive the replaceable cartridge and controllably supply air through the replaceable cartridge to generate the aerosolized matter. The appliance may include a pump for controllably supplying the air through the replaceable cartridge and a lift mechanism configured to move the replaceable cartridge to different positions within the appliance.

The lift mechanism may be configured to move the replaceable cartridge between a plurality of positions, the plurality of positions including at least a loading position wherein the replaceable cartridge can be exchanged with another replaceable cartridge and a use position wherein the replaceable cartridge can be supplied the air to generate the aerosolized matter. The appliance may further include a force sensor and the plurality of positions may further include a weigh position wherein the replaceable cartridge is positioned to rest on the force sensor to assist in determining a weight of remaining liquid within the replaceable cartridge. The lift mechanism may include a lift carriage with an air stem, the air stem being inserted in the replaceable cartridge during use to provide air to the replaceable cartridge from the pump. An air outlet of the pump may be connected to the air stem of the lift carriage by a plurality of flexible conduits including a first conduit extending from the air outlet of the pump to a bulkhead connection and a second conduit extending from the bulkhead connection to a connection on the lift carriage that is in fluid communication with the air stem. The replaceable cartridge may include an integrated circuit having at least one storage device to store cartridge data associated with the replaceable cartridge. The replaceable cartridge may include an electrical interface in electrical communication with the integrated circuit to enable retrieval of the cartridge data by a control system of the appliance which is in electrical communication with the electrical interface of the replaceable cartridge when the replaceable cartridge is installed in the appliance for use. The lift mechanism may include a lift carriage with electrical contacts arranged to interface with the electrical interface of the replaceable cartridge when the replaceable cartridge is installed in the appliance for use. The replaceable cartridge may include a cartridge housing having a plurality of housing pieces coupled together, the plurality of housing pieces including: an internal body defining the internal housing cavity partially filled with the liquid to be aerosolized; a cap fixedly coupled to the internal body and enclosing the venturi device within a combination of the cap and the internal body; and an outer casing surrounding a lower portion of the internal body.

At least one embodiment of a method implemented by a processor-based electronic liquid diffusion device may be summarized as including: receiving a signal indicative of a replaceable cartridge being received by the liquid diffusion device, the replaceable cartridge containing liquid to be aerosolized; authenticating the replaceable cartridge to ensure compatibility with the liquid diffusion device based on identification data stored by the replaceable cartridge; controlling movement of the replaceable cartridge from a cartridge loading position to an operational position after authenticating the replaceable cartridge; and controlling air flow through the replaceable cartridge to discharge aerosolized matter generated from the liquid contained in the authenticated replaceable cartridge.

The method may further include: periodically controlling the replaceable cartridge to move to a weigh position; and collecting data indicative of a level of fluid remaining in the replaceable cartridge. Collecting the data indicative of the level of fluid remaining in the replaceable cartridge may include sensing a weight of the replaceable cartridge via a sensor contained in the liquid diffusion device. The method may further include transmitting the data indicative of the level of fluid remaining in the replaceable cartridge to a client device for displaying a remaining volume of liquid to a user as the volume decreases from a full amount to an empty amount. Authenticating the replaceable cartridge may include receiving the identification data through a connection made between an electrical contact of the replaceable cartridge and a corresponding electrical contact of a lift mechanism used to move the replaceable cartridge between the cartridge loading position and the operational position. The method may further include performing a device startup routine that includes establishing a reference position of a motor to assist in controlling subsequent movement of a cartridge lift carriage driven by the motor. Establishing the reference position may include driving the cartridge lift carriage to a home position to trigger a limit switch.

At least one embodiment of a scent delivery system for controllably delivering scented aerosolized matter to an external environment may be summarized as including: a liquid diffusion appliance configured to receive a replaceable cartridge that includes a venturi device for generating the scented aerosolized matter from liquid contained within the replaceable cartridge, and configured to move air through the replaceable cartridge to assist in generating the scented aerosolized matter; one or more control circuits; one or more processors; one or more antennas; and at least one memory, the at least one memory including instructions that, upon execution by at least one of the one or more processors via at least one of the one or more control circuits, cause the scent delivery system to provide, via a user interface of a client device associated with a user of the client device, an indication of an amount of liquid remaining in the replaceable cartridge.

The instructions may further cause the scent delivery system to provide, via the user interface of the client device associated, one or more indications of information related to a power status of the liquid diffusion appliance and/or an intensity of the scented aerosolized matter being generated by the liquid diffusion appliance. The instructions may further cause the scent delivery system to provide, via the user interface of the client device, one or more indications of information related to an adjustable delivery schedule of the scented aerosolized matter, including one or more delivery time periods and one or more intensity levels associated with the one or more delivery time periods or portions thereof. The instructions may further cause the associated client device or a display of the liquid diffusion appliance to display one or more alerts related to a low amount of liquid remaining in the replaceable cartridge. The instructions may further cause the associated client device or a display of the liquid diffusion appliance to display one or more indications of information pertaining to characteristics of the replaceable cartridge or liquid contained therein, including an indication of the type of liquid contained in the replaceable cartridge. The liquid diffusion appliance may be one of a plurality of liquid diffusion devices, and each liquid diffusion appliance may be configured to provide one or more indications of information pertaining to the liquid diffusion appliance and/or a replaceable cartridge received therein to the user interface of the client device.

BRIEF DESCRIPTION OF THE SEVERAL VIEWS OF THE DRAWINGS

FIGS. 8A-8I provide representative screenshots of a user interface generated by an example application, which may run on a smartphone or other computing device paired with an air treatment appliance.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with air treatment appliances (also referred to as liquid diffusion devices), components thereof and related methods of diffusing or aerosolizing a compound from a liquid source may not be shown or described in detail to avoid unnecessarily obscuring descriptions of the embodiments. For example, embodiments of the air treatment appliances and replaceable cartridges disclosed herein may include or incorporate aspects or features of known appliances and associated components and control methods thereof. Examples of known air treatment appliances, components and aspects thereof and related methods are shown and described in U.S. Pat. Nos. 7,712,683, 7,930,068, and 8,855,827, all of which are incorporated herein by reference in their entirety.

Unless the context requires otherwise, throughout the specification and claims which follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1:
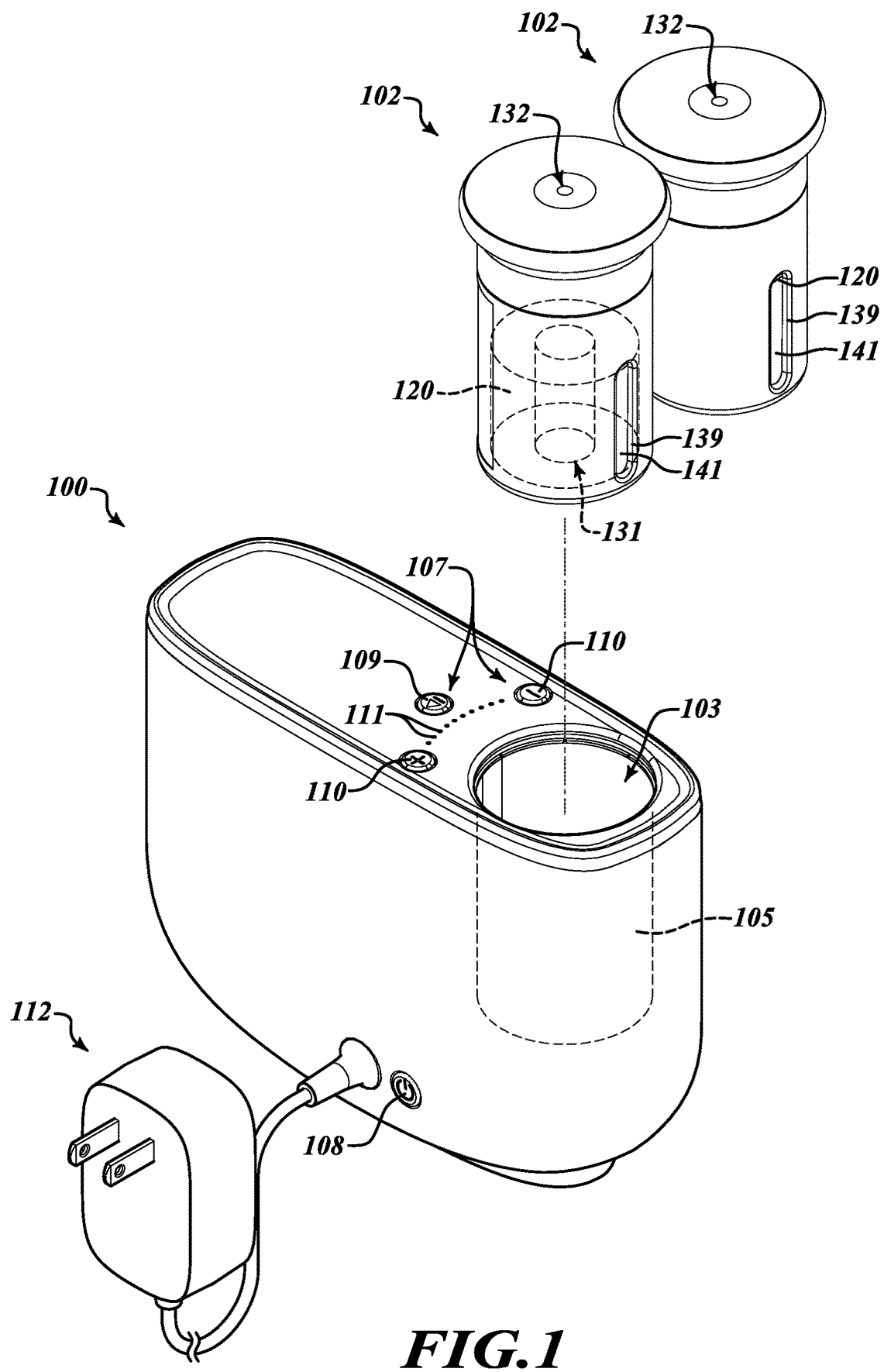
FIG. 1 is an isometric view of an air treatment appliance, according to one embodiment, for treating a space with a scent compound or other compound diffused or aerosolized from a liquid contained in replaceable cartridges that may be loaded in the appliance.
Figure 2:
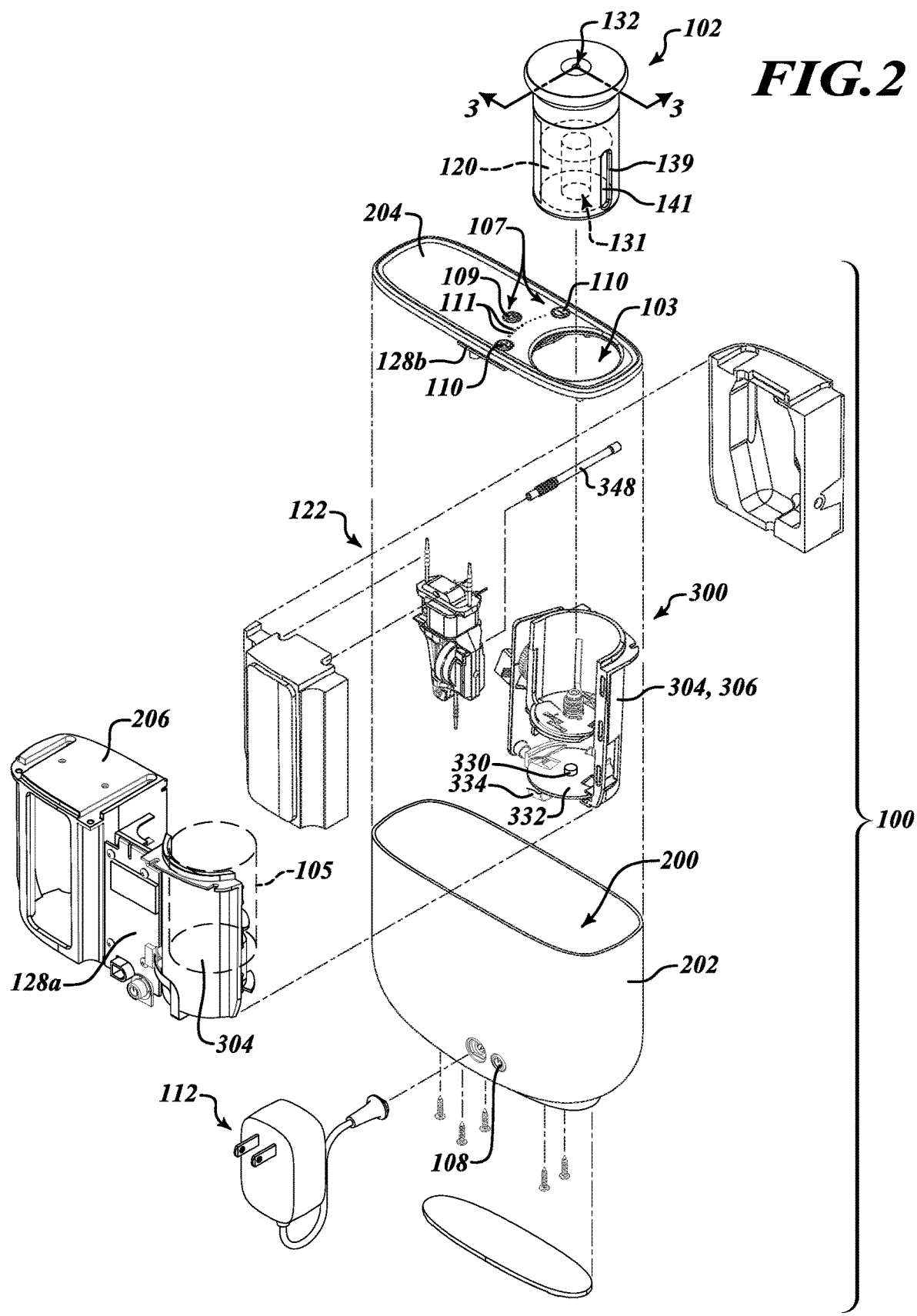
FIG. 2 is an isometric exploded view of the air treatment appliance of FIG. 1 along with a representative replaceable cartridge that is configured to generate and discharge a scent compound or other compound diffused or aerosolized from a liquid when air is controlled to move therethrough.

With reference to FIGS. 1 and 2, the present disclosure relates generally to air treatment appliances 100 and more specifically to air treatment appliances 100 including replaceable cartridges 102 containing a liquid compound to be diffused or aerosolized and released into a space to be treated, which may also referred to as liquid diffusion devices or apparatuses, and to components thereof and related methods.

As shown in FIG. 1, the air treatment appliance 100 may be provided in a tabletop form factor to rest on a table or other structure in a space (e.g., residential living space or commercial workspace) for treating the space with a scent compound or other compound diffused or aerosolized from a liquid source. The air treatment appliance 100 may also be adapted to mount on a wall or other structure to provide a wall mounted appliance. It is also appreciated that the appliance 100 may be portable in nature and may be relocated as desired to treat different spaces as desired.

With reference to FIGS. 1 and 2, the replaceable cartridge 102 includes a cartridge outlet 132 to permit a diffused or aerosolized compound generated from the liquid 120 within the cartridge 102 to be discharged into the environment or space surrounding the appliance 100. More particularly, when loaded, the replaceable cartridge 102 within the appliance 100 is coupled to an outlet of a source of pressurized air (e.g., pump assembly 122 of FIG. 2) to enable pressurized air to be selectively passed through the cartridge 102 as described herein to diffuse or aerosolize the liquid 120 contained therein and to force the aerosolized matter to be discharged through the cartridge outlet 132.

Within the present disclosure, the terms atomize and diffuse may be used in their various forms interchangeably. They are intended to refer to generally the same action, that being the dispersion of liquid into very small particle sizes (preferably but not limited to one micron or less in size) and releasing the particles into the atmosphere of a generally enclosed space. Discharging diffused liquid with particularly small particles helps ensure that the liquid to be dispersed remains airborne long enough to effectively treat the space. The diffused liquid is also referred to herein as aerosolized matter, and may include, for example, a scented compound.

One approach to providing small particle sizes is to incorporate a dispersion or gas-liquid mixing location adjacent an expansion chamber. The mixed gas and liquid combination may contain particles of greater than desirable size. Allowing this mix to remain resident within the expansion chamber prior to release into the treated space will allow larger particles to precipitate out of the mixture. Structures that the gas and liquid mixture impinge upon may also assist in the collection of these larger particles and leave only the desired predominantly smaller sized particles to be released. The expansion chamber may be maintained at a positive pressure with respect to the atmospheric pressure within the space to be treated, so that the gas and liquid mix will be ejected from the appliance 100 into the space. Alternatively, the expansion chamber may generally be maintained at the atmospheric pressure of the space to be treated with the flow of gas (e.g., air) through the chamber providing the impetus for movement of the gas and liquid mix from the cartridge 102 of the appliance 100 into the space to be treated.

Within the context of this disclosure, diffusion or aerosolizing also generally refers to a process or method of dispersing a liquid without destroying the integrity of the liquid compound. While some degree of reactivity between the gas (e.g., air) and the liquid may be desirable, diffusion generally does not change the nature of the liquid, unlike heating or the application of electrical energy into the liquid to diffuse the liquid.

The air treatment appliances 100, replaceable cartridges 102 and other components and methods described herein may be used to provide or introduce a pleasant or soothing scent (or some other type of liquid that may be used as an airborne treatment or compound) into the air space of a room or other generally enclosed space. The particular liquid 120 to be dispensed by the diffusion device is contained within the replaceable cartridge 102. Other possible types of liquids that may be dispersed may include decontamination agents, insecticides, insect repellents, and many different types of liquids that may be desirably dispersed within an enclosed space. The present disclosure is not limited to a particular type or nature of liquid 120 to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space. Larger spaces, such as concert halls, casinos, lobbies, etc., may have one or more openings into the space and still have the desired characteristics to permit treatment with a diffused liquid. Other spaces may be preferably fully enclosed to permit treatment by the selected liquid. In other cases, the liquid used for treatment may preferably be used in a sealed space, for maximum effectiveness or for safety reasons. Within the scope of the present disclosure, it is not intended to limit the nature, size or configuration of the space to be treated except as may be appropriate for the liquid used to treat the space and the nature of treatment desired within the space.

With reference to FIG. 2, and according to the illustrated embodiment, a control system 128*a*, 128*b* (collectively 128) is provided and is configured to permit adjustment of the timing, flow rate and/or pressure level of the pressurized air generated by a pump assembly 122 that is directed into and passes through an installed cartridge 102 during use. In some instances, the operating pressure may be relatively low, such as, for example, less than about 2 psi gauge pressure or about 1.5 psi gauge pressure. Within the cartridge 102, the pressurized air is directed to atomize the liquid 120 contained therein and to aid in the dispersion of the atomized liquid into the air space to be treated.

In some instances, it may be desirable to have an indirect route from the point of actual atomization of the liquid and a cartridge outlet 132 through which atomized particles exit from the cartridge 102. As will be described in greater detail elsewhere, embodiments of the replaceable cartridges 102 described herein provide an atomization zone where liquid 120 from the cartridge 102 and pressurized air meet and are mixed. In addition, the cartridges 102 may also provide an expansion chamber or chambers within the cartridge 102 where the atomized liquid is retained until a portion of the atomized liquid is allowed to exit the cartridge 102 loaded in the host appliance 100. As described in greater detail elsewhere, the cartridges 102 may combine storage of the liquid 120 to be diffused, an atomization structure to transform the liquid 120 into an airborne concentration, an expansion chamber or chambers, and optionally a tortuous path or passage towards the outlet 132 of the cartridge 102.

With reference to FIGS. 1 and 2, one example embodiment of an air treatment appliance 100 is illustrated and includes an appliance housing 101 and replaceable cartridges 102 to be selectively installed therein. As previously discussed, the appliance 100 is configured to treat a space with a diffused or aerosolized compound generated by a flow of air moving through the cartridge 102 which is entrained with liquid particles from liquid 120 contained in the cartridge 102. For this purpose, the appliance 100 may include a plurality of controls 107, such as, for example, a power on/off control 108 for powering up and powering down the appliance 100, a play/pause control 109 for activating and deactivating air treatment programs for discharging aerosolized matter into the surrounding environment, and intensity controls 110 for adjusting the intensity or quantity of discharged matter into the surrounding environment. The appliance 100 may further include one or more indicators 111 (e.g., LEDs) for providing operational feedback signals, such as, for example, an intensity level at which the appliance 100 is operating. The appliance 100 may further include a power unit 112 for connecting the appliance 100 to a power outlet. In other embodiments, the appliance 100 may include an onboard power supply, such as an onboard rechargeable battery or battery pack, to facilitate use of the appliance 100 in a location that may be remote from a power outlet or other external power source.

Figure 3:
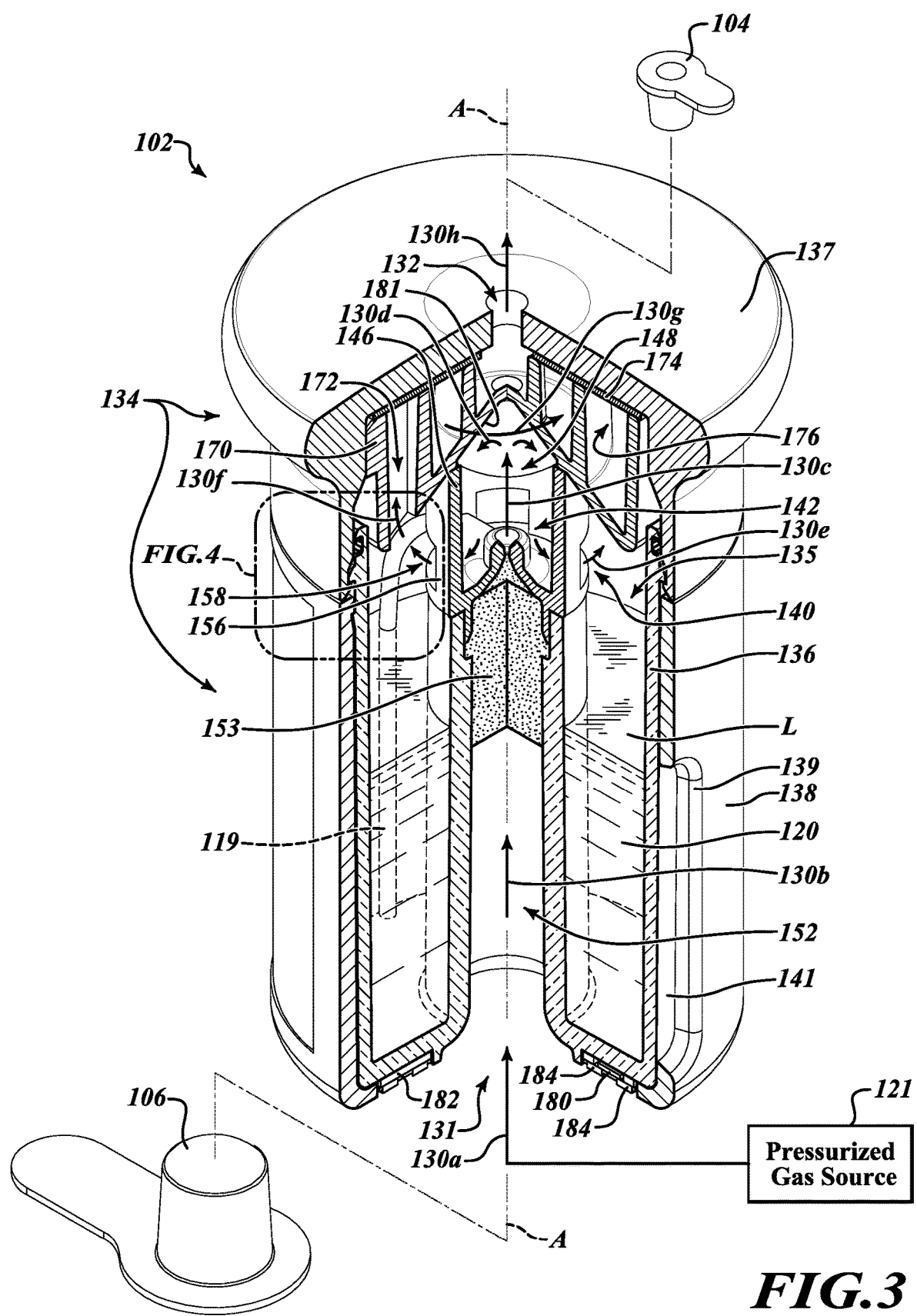
FIG. 3 is an isometric cross-sectional view of the replaceable cartridge shown in FIG. 3 taken along section lines 3-3.

With reference now to FIG. 3, the replaceable cartridge 102 may include a cartridge housing 134 comprising a plurality of housing pieces coupled together to define a fluid receptacle having an internal cavity 135, which is partially filled with the liquid 120 to be diffused. For example, in accordance with the example embodiment of the cartridge 102 shown in FIG. 3, the cartridge housing 134 includes an internal housing body 136 defining at least a portion of a receptacle for the liquid 120 to be aerosolized, an upper housing cap 137 including the cartridge outlet 132 through which the aerosolized matter is discharged during use, and an outer casing 138 surrounding at least a lower portion of the internal housing body 136. In some instances, the at least some of the housing pieces, for example, the internal housing body 136 and the upper housing cap 137, may be fixedly coupled together to prevent non-destructive disassembly of the cartridge 102, making it effectively tamperproof. This may be desirable to prevent users from refilling and reusing a spent cartridge that may be ineffective or less effective in treating the space due to fouling or build-up of residue within the cartridge 102 from prior use.

Figure 4:
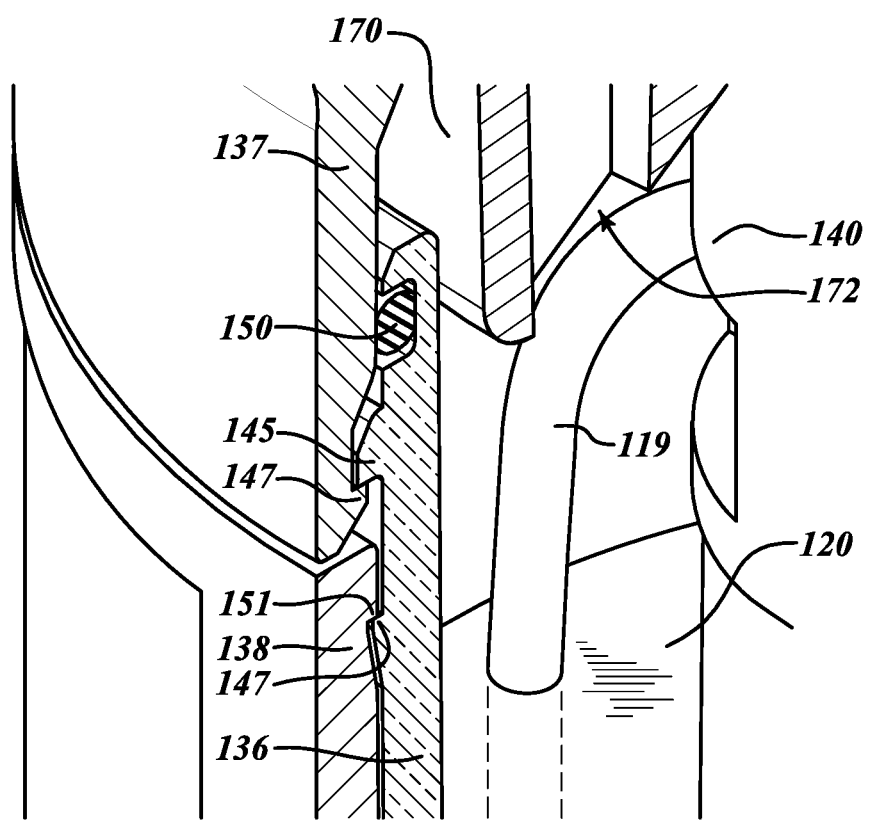
FIG. 4 is an enlarged detail view of a portion of the cross-sectional view of the replaceable cartridge of FIG. 3 showing various coupling arrangements provided to join housing components of the cartridge together.

As an example, and with reference to FIGS. 3 and 4, the internal housing body 136 and the upper housing cap 137 may be provided with interlocking structures 145, 147 that snap or otherwise couple together in a manner that prevents non-destructive disassembly of the cartridge housing 134. A seal 150, such as an o-ring seal or other seal, may be provided between the internal housing body 136 and the upper housing cap 137 near the interlocking structures 145, 147 to provide a liquid tight seal when the cartridge housing 134 is assembled. In this manner, the liquid 120 to be diffused may be prevented from leaking from the cartridge housing 134 at an interface between the internal housing body 136 and the upper housing cap 137. Upon depletion of the liquid 120, the cartridge 102 may be readily removed and replaced with a like cartridge 102 for continued treatment of the environment surrounding the host appliance 100, and the depleted cartridge 102 may be discarded as an intact unit or collected for refurbishment purposes.

With continued reference to FIGS. 3 and 4, the internal housing body 136 and the outer casing 138 may be provided with interlocking structures 149, 151 that couple together in a manner that prevents disassembly of the outer casing 138 from the internal housing body 136 until a threshold resistive force is overcome, after which the outer casing 138 may be removed from the internal housing body 136. In other instances, the interlocking structures 149, 151 may prevent non-destructive disassembly of the outer casing 138 from the remainder of the cartridge 102 to further assist in making the cartridge 102 tamperproof.

In accordance with the example embodiment of the replaceable cartridge 102 shown in FIG. 3, the internal housing body 136 may be transparent or semi-transparent and the outer casing 138 may be opaque, and the outer casing 138 may be provided with a window 139 through which a level L of the liquid 120 to be aerosolized is viewable through an exposed portion 141 of the transparent or semi-transparent internal housing body 136. Advantageously, the window 139 of the outer casing 138 may have a size and a shape sufficient to observe the liquid level L of the liquid 120 in the internal housing body 136 as the liquid 120 transitions between a full level and an empty level. In this manner, a user can retrieve the cartridge 102 from the appliance 100 as desired and check the level of liquid 120 therein. As described in further detail elsewhere, additional functionality may be provided in connection with the appliance 100 for sensing a level of the liquid 120 in an installed cartridge throughout operation. Although the cartridge housing 134 of the example cartridge 102 includes a liquid level viewing window 139, in some embodiments, a replaceable cartridge may be provided without such a window 139. In addition, the outer casing 138 may be omitted altogether. When provided, the outer casing 138 may have a shape that nests closely with the internal housing body 136. For example, the outer casing 138 and the internal housing body 136 may each have a substantially cylindrical shape concentrically aligned forming a dual layer or dual wall receptacle.

With continued reference to FIG. 3, the internal housing body 136, upper housing cap 137, and outer casing 138 may be fixedly coupled together to define the cartridge housing 134. A cartridge inlet 131 may be provided at a bottom end of the internal housing body 136 to receive a flow of gas (e.g., air) during operation and the cartridge outlet 132 may be provided in the upper housing cap 137 for discharging diffused liquid generated by the cartridge 102 during operation. The cartridge inlet 131 and the cartridge outlet 132 may be aligned along a central axis A defined by the cartridge housing 134. The cartridge housing 134 may be generally rotationally symmetric about the central axis A. For example, as shown in FIG. 3, the cartridge housing 134 may resemble a cylinder or similar receptacle with a mushroom or enlarged top end that is rotationally symmetric about the central axis A. In other instances, the cartridge housing 134 may be asymmetrically shaped and the cartridge inlet 131 and cartridge outlet 132 may not be aligned vertically along a common axis A. Respective caps or plugs 104, 106 may be provided to temporarily close the cartridge inlet 131 and cartridge outlet 132 during storage, transport or the like to prevent fouling or contamination of the cartridge 102 or possible leakage of the liquid 120 contained therein.

Internal components and structures of the cartridge 102 and related functionality will now be described with continued reference to FIGS. 3 and 4, some of which generally track similar features and functionality disclosed in U.S. patent application Ser. No. 14/612,066, filed Feb. 2, 2015, now issued as U.S. Pat. No. 9,248,461, and U.S. patent application Ser. No. 14/612,072, filed Feb. 2, 2015, now issued as U.S. Pat. No. 9,162,004, which are incorporated by reference in their entireties. According to the illustrated embodiment of the cartridge 102 shown in FIGS. 3 and 4, the internal components and structures provide, among other things, a flow path through the cartridge 102 from the cartridge inlet 131 to the cartridge outlet 132, as represented by the arrows labeled 130a-130h. When installed in the host diffusion appliance 100, the cartridge inlet 131 is coupled to a source of pressurized gas 121 (e.g., pump 122 of FIG. 2) such that the gas (e.g., air) may be periodically forced through the cartridge 102 as generally represented by the arrows labeled 130a-130h to combine with the liquid 120 and to exit as a gas-liquid mixture comprising particularly small liquid particles carried by the gas, referred to generally herein as a diffused liquid or aerosolized matter. Details of the example pump 122 are not shown or described herein to avoid unnecessarily obscuring descriptions of the embodiments; however, it will be appreciated that the pump 122 may be provided in a wide variety of different form factors, including, for example, the pump assemblies shown and described in U.S. patent application Ser. No. 14/693,716, filed Apr. 22, 2016, now issued as U.S. Pat. No. 9,358,562, which is also incorporated herein by reference in its entirety.

As shown in FIG. 3, the pressurized gas enters the cartridge 102 through the cartridge inlet 131 at a bottom end of the housing 134 and then flows through a diffusion head 140 provided within the housing 134, which includes a venturi device 142 for drawing the retained liquid 120 into the moving gas stream through an intake conduit 119, after which the gas-liquid mixture moves through a cartridge insert 170 before exiting the cartridge 102 through the cartridge outlet 132. More particularly, the pressurized gas enters the cartridge 102 through the cartridge inlet 131 at a bottom end of the housing 134, as represented by the arrow label 130a, and then flows upwardly through a gas supply conduit 152 defined by a portion of the internal housing body 136, as represented by the arrow labeled 130b. The gas then flows through the venturi device 142 drawing in liquid 120 from a fluid reservoir within the internal housing cavity 135 of the housing 134 via the intake conduit 119 to create a gas-liquid mixture comprising atomized liquid (also referred to herein as diffused liquid or aerosolized matter) that is discharged into an expansion chamber 148 provided by an upper portion 146 of the diffusion head 140, as represented by the arrow labeled 130c. The diffused liquid is then directed toward an impact structure or surface 181 located opposite the venturi device 142 wherein at least some of the diffused liquid impacts and collects on the impact structure or surface 181 and is routed back to any remaining liquid 120 in the fluid reservoir to be reintroduced into the gas stream by the venturi device 142. At least some other of the diffused liquid is redirected to flow down around bulkhead portions 156 of the diffusion head 140 and to pass through passageways 158 in the diffusion head 140 leading to a portion of the internal cavity 135 of the cartridge housing 134 above the fluid level L of liquid 120 in the cartridge 102, as represented by the arrows labeled 130d and 130e. From there, some of the diffused liquid may collect on the exposed interior surfaces of the housing 134 or other internal structures of the cartridge 102, or otherwise precipitate out of the gas and atomized liquid, and rejoin the liquid 120 in the fluid reservoir to be reintroduced into the gas stream by the venturi device 142. Some other of the diffused liquid may be propelled into the cartridge insert 170 via an inlet 172 thereof, as represented by the arrow labeled 130f. From the inlet 172 of the insert 170, the diffused liquid proceeds along a tortuous passage (e.g., a spiral passage) through the cartridge insert 170, as represented by the arrow labeled 130g, before passing through an outlet zone of the insert 170 and ultimately the cartridge outlet 132 to be discharged from the cartridge 102, as represented by the arrow labeled 130h. In making this convoluted journey from the expansion chamber 148 to the cartridge outlet 132, the liquid particle size distribution of the diffused liquid is refined such that only particularly fine particles are successfully discharged from the cartridge 102 with relatively larger particles collecting on one or more surfaces of the internal structures and components of the cartridge 102, or otherwise precipitating out of the gas, for rejoinder with remaining liquid 120 in the liquid reservoir for reintroduction into the gas stream passing through the venturi device 142.

With continued reference to the example embodiment of the replaceable cartridge shown in FIG. 3, it will be appreciated that the cartridge housing 134 and internal components of the cartridge 102 may define a plurality of distinct chambers downstream of the venturi device 142 through which the diffused liquid sequentially travels before being discharged from the cartridge 102 and ultimately into a surrounding environment. More particularly, the upper portion 146 of the diffusion head 140 and a lower portion of the insert 170 may define a primary expansion chamber 148 immediately above the venturi device 142, a secondary chamber may be provided external of the diffusion head 140 and the insert 170 within the internal cavity 135 of the housing 134 above the fluid level L of the liquid 120 to be diffused, and a tertiary chamber may be provided by the tortuous passage 176 of the insert 170. Passageways or apertures 158 in the upper portion 146 of the diffusion head 140 provide fluid communication between the primary expansion chamber 148 and the secondary chamber. The upper portion 146 of the diffusion head 140 also defines a bulkhead or bulkhead portions 156 that impede the diffused liquid generated by the venturi device 142 from exiting the primary expansion chamber 148 other than through the plurality of passageways or apertures 158. The inlet 172 of the insert 170 provides fluid communication between the secondary chamber and the tertiary chamber (i.e., the tortuous passage 176). Although only one inlet 172 and one tortuous passage 176 is shown providing the sole passage for the diffused liquid to exit the cartridge 102, it is appreciated that a plurality of inlets 172 may be provide to enable diffused liquid to enter one or more tortuous passages leading to the outlet 132 of the cartridge 102. A gasket 174 may also be positioned between an upper end of the insert 170 and the upper housing cap 137 with the gasket 174 forming a cover over the tortuous passage 176.

The distinct chambers described above (i.e., the primary expansion chamber, the secondary chamber and the tertiary chamber) may collectively assist in refining the composition of the diffused liquid to include only the finest liquid particles as the diffused liquid moves sequentially through the chambers during operation. For instance, by the time the gas-liquid mixture exits from cartridge 102, there has been some residence time in each of the distinct chambers to permit undesirably large liquid particles or droplets to precipitate out of or otherwise separate from the mixture and be returned to the liquid reservoir within the internal cavity 135 of the housing 134 for later atomization and dispersion. In this manner, the removable cartridge 102 and components thereof may provide a cartridge solution for a liquid diffusion appliance 100 which has an efficient form factor that is particularly effective at treating spaces with diffused liquid having extremely small liquid particles.

With continued reference to FIG. 3, a liquid retention device 153, such as, for example, an open cell foam plug, may be positioned within the gas supply conduit 152 adjacent the venturi device 142 to retain liquid 120 that may pass downward through the venturi device 142 into the gas supply conduit 152. This may occur during shipping as liquid 120 may move through the intake conduit 119 into the venturi device 142 and unwantedly into the gas supply conduit 152. In addition, it may occur when stopping the flow of air through the cartridge 102 which may result in some of the liquid expelled into the expansion chamber 148 settling back down into and passing through the venturi device 142. The liquid retention device 153 may collect liquid 120 that unwantedly passes into the gas supply conduit 152 and retain the liquid 120 therein until the cartridge 102 is used again, at which time the air flowing through the cartridge 102 may clear the liquid 120 from the liquid retention device 153.

With continued reference to FIG. 3, the replaceable cartridge 102 may further comprise an integrated circuit 180 coupled to the cartridge housing 134, the integrated circuit including memory to store cartridge data associated with the replaceable cartridge 102. The cartridge data may include, for example, a type of liquid 120 stored in the cartridge 102, an amount of liquid 120 stored in the cartridge, a cartridge identifier from which to authenticate the cartridge 102, and/or other data. The amount of liquid 120 may be measured directly, indirectly or otherwise estimated by usage history data or other techniques. For example, duration and intensity history data associated with the operation of the host appliance 100 and a particular cartridge 102 may be logged and used to estimate the amount of liquid 120 remaining in the cartridge 102. In other instances, a weight of the liquid 120 may be directly or indirectly measured periodically to provide fluid level feedback functionality as described in more detail elsewhere. In still other instances, it is contemplated that the fluid level may be measured using an optical sensor or other techniques for observing the boundary between the liquid 120 and air space above the liquid 120 within the cartridge.

As shown in FIG. 3, the integrated circuit 180 may be embedded in or otherwise coupled to a cartridge printed circuit board (PCB) 182. The cartridge PCB 182 may be coupled to the cartridge housing 134, such as, for example, by adhesive or other joining techniques or devices. According to the example embodiment of the cartridge 102 shown in FIG. 3, the cartridge PCB 182 is located at a bottom end of the cartridge housing 134 and has an annular shape that nests with the bottom end of the cartridge housing 134. The cartridge PCB 182 further comprises an electrical interface 184 in electrical communication with the integrated circuit 180 to enable retrieval of the cartridge data by an external system contacting the electrical interface 184. According to the example embodiment, the electrical interface 184 includes a pair of annular conductors that are provided on a lower exposed face of the cartridge PCB 182 and are arranged to make contact with corresponding contacts 356 (FIGS. 5 and 6) provided in the appliance 100. The electrical interface 184 further includes at least one contact surface to mechanically couple the electrical interface 184 with at least one circuit contact surface of the integrated circuit 180 such that the control system 128 of the appliance 100 is able to communicate with the integrated circuit 180 and retrieve data from and optionally send data to the integrated circuit 180 via the electrical interface 184. Although the example embodiment of the cartridge 102 shown in FIG. 3 includes an integrated circuit 180 that is configured to communicate through a physical electrical connection (e.g., electrical interface 184), it is appreciated that in some embodiments, the integrated circuit 180 may be configured for contactless communication with the control system 128 of the host appliance 100, such as, for example, by including a rewriteable microchip that can be transcribed via radio waves.

Further details of the air treatment appliance 100 and components thereof will now be described with reference to FIGS. 2, 5 and 6. As previously described, the air treatment appliance 100 includes a replaceable cartridge 102 containing liquid 120 to be aerosolized and discharged through a cartridge outlet 132, a pump assembly 122 operatively coupled to the replaceable cartridge 102 to supply air to the replaceable cartridge 102 to generate the aerosolized compound from the liquid 120, a control system 128 operatively coupled to the pump assembly 122 for controlling the pump assembly 122 to supply the air to the replaceable cartridge 102 to generate the aerosolized compound and discharge the aerosolized compound from the cartridge outlet 132, and an appliance housing 101 that accommodates the replaceable cartridge 102, the pump assembly 122 and the control system 128 therewithin.

As shown in FIG. 2, the appliance housing 101 of the example embodiment includes a base housing 202 and a cover 204 coupleable to the base housing 202 to define an internal cavity 200 within which components of the appliance 100, such as, pump 122, are accommodated. The appliance housing 101 may further include one or more internal housing components, such as, for example, a chassis 206, for supporting various functional components of the appliance 100. The functional components may include, for example, the pump 122, one or more components of the control system 128a, and a lift mechanism 300 for moving the replaceable cartridge 102, when installed, between different positions. With reference to FIGS. 1 and 2, the appliance housing 101 may define or include a cartridge port 103 through which to receive the replaceable cartridge 102 and a cartridge cavity 105 cavity extending into the appliance housing 101 from the cartridge port 103 within which the replaceable cartridge 102 is received during use, and within which the position of the replaceable cartridge 102 may be adjusted by the lift mechanism 300.

Figure 5:
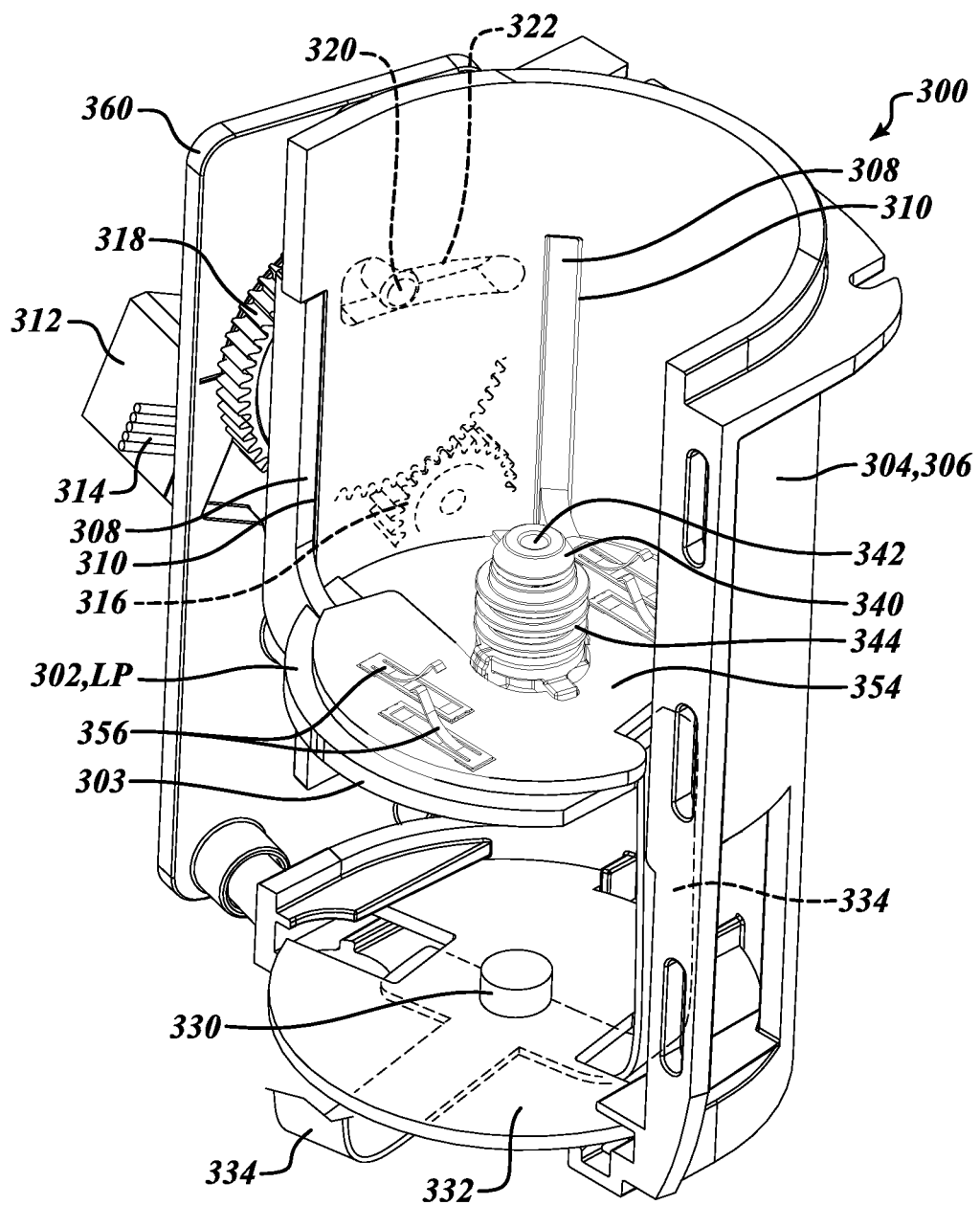
FIG. 5 is an isometric view of a lift mechanism, according to one embodiment, for moving a replaceable cartridge, when loaded, between different positions, including a loading position and an operational position.
Figure 6:
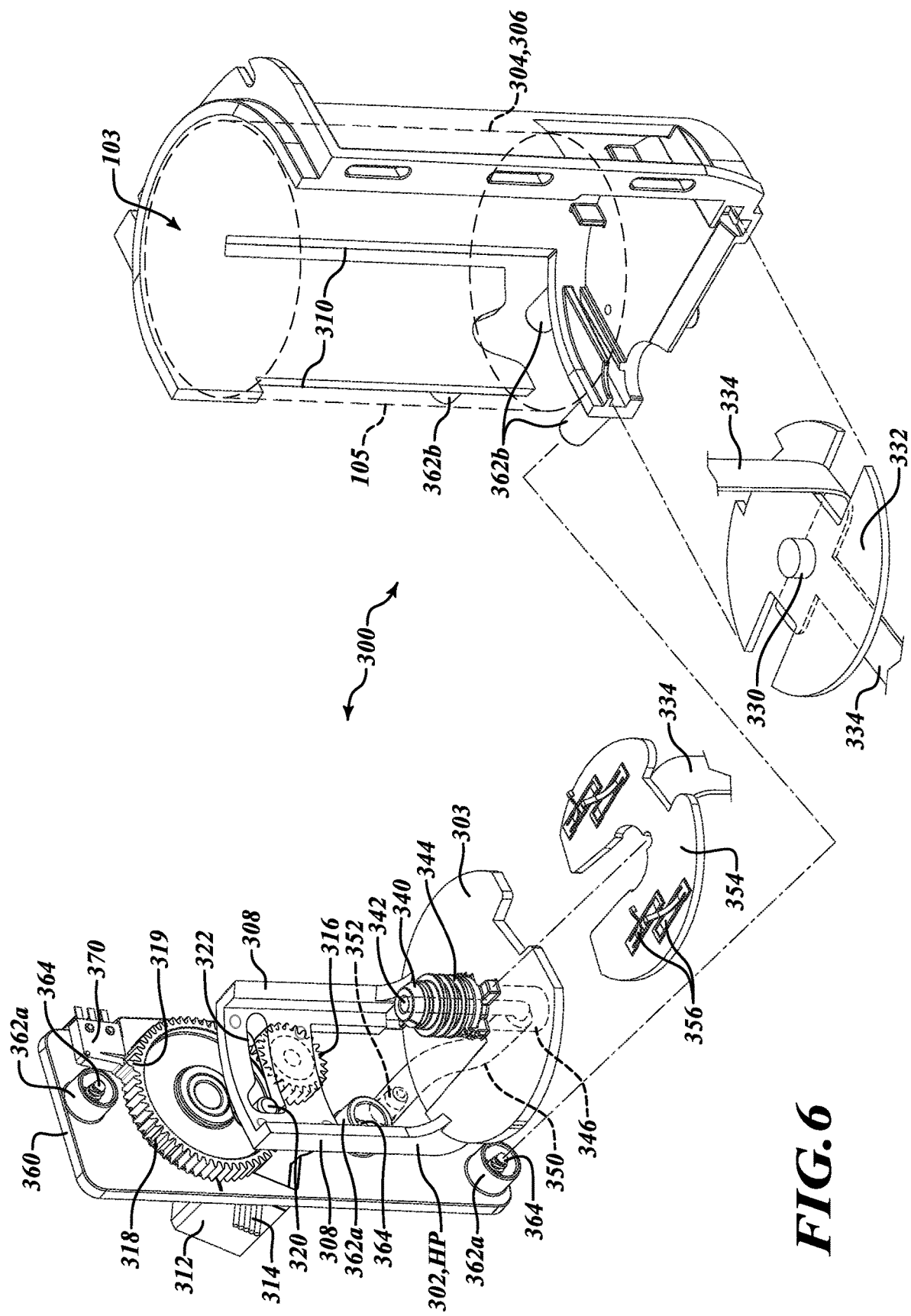
FIG. 6 is a partially exploded isometric view of the lift mechanism of FIG. 5 showing additional details of the lift mechanism.

FIGS. 5 and 6 show additional details of the example embodiment of the lift mechanism 300, which is coupled to the chassis 206 and accommodated within the internal cavity 200 of the appliance housing 101. FIG. 5 shows the lift mechanism 300 in an assembled state with a lift carriage 302 thereof located at a loading position LP wherein the replaceable cartridge 102 may be installed in the appliance 100. FIG. 6 shows the lift mechanism 300 in a partially exploded state with the lift carriage 302 thereof located at a home position HP, which may be used at startup to provide indexing functionality for system controls, to assess the liquid level in the cartridge 102, or to facilitate other functionality.

With reference to FIGS. 2, 5 and 6, the lift mechanism 300 includes or otherwise operates in conjunction with a lift enclosure 304, which may be formed at least in part by the chassis 206 of the appliance housing 101, another internal housing piece, and/or a separate lift enclosure component 306. For example, a portion of the chassis 206 and a separate lift enclosure component 306 may join together in a friction fit, interference fit or snap fit to form a lift enclosure 304 which defines the cartridge cavity 105 within which the replaceable cartridge 102 is received during use, and within which the position of the replaceable cartridge 102 may be adjusted by the lift mechanism 300. For this purpose, the chassis 206 and the separate lift enclosure component 306 may include various coupling arrangements, such as resilient projections or tabs and corresponding apertures, which enable the components to be joined together without separate fasteners. In other instances, separate fasteners or other joining techniques may be used to form the lift enclosure 304.

With continued reference to FIGS. 2, 5 and 6, the lift mechanism 300 of the example embodiment includes the lift carriage 302. The lift carriage 302 is configured to removably receive the replacement cartridge 102 and to move up and down within the cartridge cavity 105 with the replacement cartridge 102 supported thereon. The lift carriage 302 may include, for example, rails 308 that constrain the lift carriage 302 to translate back and forth within the cartridge cavity 105 within tracks 310 of the lift enclosure 304. In this manner, the lift carriage 302 may operate akin to an elevator in an elevator shaft.

With reference to FIGS. 5 and 6, the lift mechanism 300 of the example embodiment further includes a motor 312 (e.g., an electric stepper motor) in communication with a motor controller (not shown) of the control system 128 via electrical leads 314, which is operable to drive the lift carriage 302 between different positions within the cartridge cavity 105. For this purpose, the example embodiment includes a pinion 316 attached to a drive shaft of the motor 312 which is in meshed engagement with a gearwheel 318. The gearwheel 318 includes a lift pin 320 extending therefrom which projects into a lift cavity 322 provided within the lift carriage 302. The interaction of the lift pin 320 with the lift cavity 322 through rotation of the drive motor 312, pinion 316 and gearwheel 318 causes the lift carriage 302 to move up and down within the cartridge cavity 105. The example embodiment of the lift mechanism 300 shown in FIGS. 5 and 6 is configured to move the lift carriage 302 at least between a cartridge loading position LP, shown in FIG. 5, wherein the lift pin 320 may be at located at top dead center of the rotational position of the gearwheel 318 and an operational position (not shown) wherein the lift pin 320 may be located at bottom dead center of the rotational position of the gearwheel 318. The lift mechanism 300 may be further configured to move the lift carriage 302 to a home position HP (or weighing position), wherein the lift pin 320 is caused to lose contact with the structure of the lift carriage 302 surrounding the lift cavity 322 such that the lift carriage 302 is temporarily disengaged from the drive motor 312 and intermediate drive train components (e.g., pinion 316 and gearwheel 318).

According to some embodiments, a force sensor 330 may be provided in the cartridge cavity 105 and may be arranged such that the lift carriage 302 comes to rest upon the force sensor 330 when in the home position HP (or weighing position), such that the force sensor 330 may be used to collect data indicative of a weight of the liquid 120 remaining in a replaceable cartridge 102 supported by the carriage 302. This may be done by subtracting out the amount of force attributed to the lift carriage 302 and to the cartridge 102 when empty. In this manner, the lift carriage 302 may be driven to the home/weighing position as desired to detect the weight and hence amount of liquid 120 remaining in the cartridge 102 at any time. This information may then be stored in memory of the control system 128 and used to provide enhanced functionality such as, for example, alerts pertaining to liquid 120 in the cartridge 102 running low. This may include a visual display of one or more alerts on the appliance 100 itself or another device, such as a smartphone, that may be paired with or otherwise associated with the appliance 100. The fluid level feedback functionality may also enable auto-replenishment of the cartridges 102, such as re-ordering of one or more replacement cartridges 102 when the installed cartridge 102 hits a certain amount of remaining liquid 120 (e.g., 10% of full capacity). Fluid level feedback may also enable the appliance 100 to optimize various control parameters, such as the flow velocity of the supplied air to the cartridge 102, based at least in part on the amount of remaining liquid 120 in the cartridge 102. To facilitate such functionality, the force sensor 330, when provided, may be mounted to a circuit board 332 at a bottom end of the lift enclosure 304, which may form a part of the control system 128 or otherwise communicate with the control system 128, such as, for example, via a flex circuit component 334 or other electrical lead.

With reference to FIGS. 5 and 6, the lift carriage 302 of the example embodiment includes an air stem 340 having an air passageway 342 for communicating a flow of air from an air source (e.g., pump 122 of FIG. 2) into the replaceable cartridge 102 when installed for use. For this purpose, the air stem 340 may include a seal arrangement 344 that is sized and shaped to sealingly engage the gas supply conduit 152 of the replacement cartridge 102 when the cartridge 102 is pressed onto the air stem 340 to be supported by the lift carriage 302 during use. The air stem 340 may be in fluid communication with an air coupling 346 (e.g., nipple or other coupling) on an opposing side of a base platform 303 of the lift carriage 302. The air coupling 346 may be configured to receive the flow of air from one or more air supply conduits 348, 350 connected to the air supply. For example, a first supply conduit 348 may extend from an outlet of the air supply (e.g., outlet of pump 122) to a bulkhead connection 352 and a second air supply conduit 350 may extend from the bulkhead connection 352 to the air coupling 346 on the lift carriage 302. At least the second air supply conduit 350 may be provided as a flexible conduit to account for movement of the lift carriage 302 throughout its range of motion. Although the example embodiment is illustrated as having two separate air supply conduits 348, 350 joined together at a bulkhead connection 352, it is appreciated that a single conduit may be used or to route air to the cartridge 102, or that more than two conduits may be used.

With reference to FIGS. 2, 5 and 6, the lift mechanism 300 may further include a lift carriage circuit board 354 with exposed electrical contacts 356, which are configured to make contact with the electrical interface 184 provided on the bottom of the replaceable cartridges 102 provided for use with the appliance 100. The lift carriage circuit board 354 may form part of the control system 128 or otherwise communicate with the control system 128, such as, for example, via a flex circuit component 334 or other electrical lead. The flex circuit component 334 or other electrical lead may be designed and arranged to account for the movement of the lift carriage 302 through its range of motion.

With continued reference to FIGS. 2, 5 and 6, the lift mechanism 300 may further include a bulkhead 360 for mounting the motor 312 and other lift mechanism components in a suitable position for driving the lift carriage 302 as described herein. The bulkhead 360 may be coupled to a side of the lift enclosure 304 by suitable joining techniques, such as, for example, connection bosses 362a, 362b and corresponding threaded fasteners 364. The bulkhead 360 may provide a suitable fixed connection (e.g., bulkhead connection 352) for assisting in routing air to the replaceable cartridge 102 during use and minimizing movement of the air supply conduit 350 as the fore end of the air supply conduit 350 moves with the lift carriage 302. The bulkhead 360 may also provide a mounting location for a limit switch 370 that may be arranged relative to the lift carriage drive components to sense when the lift carriage 302 has been driven to the home position HP, as shown in FIG. 6. The limit switch 370 may be in electrical communication with the control system 128 to provide an indexing function at startup for determining a rotational position of the drive motor 312 from which to base subsequent movements of the lift carriage 302. In other instances, a motor having positional feedback may be used such that indexing of the motor 312 is not needed. As shown in FIG. 6, the gearwheel 318 may include a projection 319 arranged to trip the limit switch 370 when the lift carriage 302 reaches the home position HP, or other chosen position.

Figure 7:
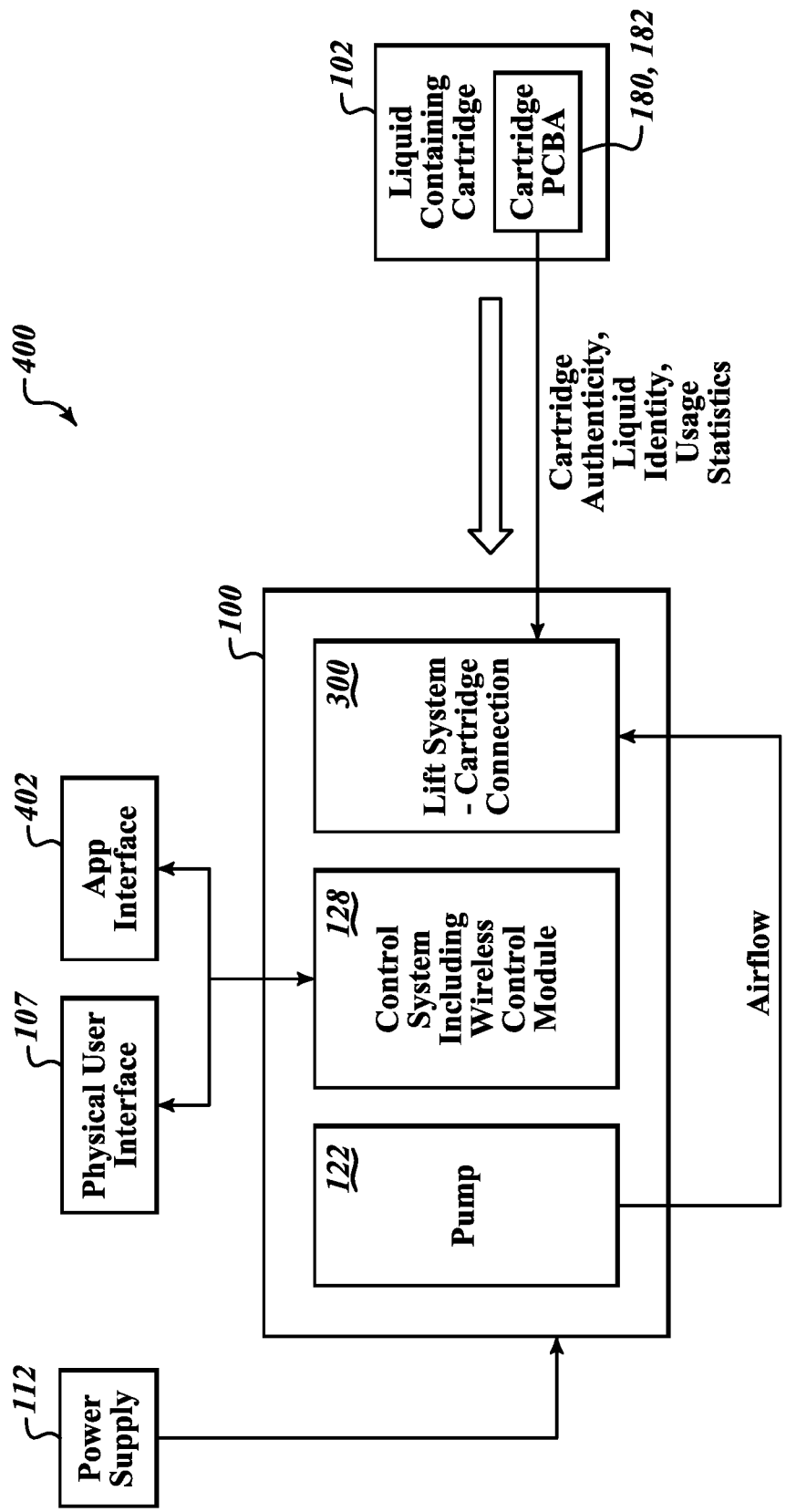
FIG. 7 is a system diagram, according to one example embodiment, of an air treatment system which includes an air treatment appliance and a replaceable cartridge therefor.

FIG. 7 provides a system diagram, according to one example embodiment, of an air treatment system 400 comprising an air treatment appliance, such as, for example, the example embodiment of the air treatment appliance 100 described above with reference to FIGS. 1 through 6, and a replaceable cartridge installable in the appliance 100 and containing a liquid to be discharged as aerosolized matter, such as the replaceable cartridge 102 shown in FIGS. 1 through 4. As can be appreciated from a review of FIG. 7, the appliance 100 may include a control system 128 that is configured to receive one or more control inputs from a physical user interface (e.g., controls 107) of the appliance 100 and/or an application interface 402, which may be provided via a smartphone or other computing device to control the appliance 100 remotely. The control system 128 is operatively coupled to a lift mechanism 300 that is configured to receive an installable cartridge 102 containing liquid to be discharged by the appliance 100, and to move the cartridge 102 among different operating positions. The control system 128 is also operatively coupled to an air source (e.g., pump 122) for supplying air flow through the cartridge 102 for generating the aerosolized matter from the liquid contained in the cartridge 102 for discharge into the surrounding environment. The cartridge 102 includes a cartridge PCB 182 and an associated integrated circuit 180 for storing cartridge information and enabling the transfer of information between the cartridge 102 and the control system 128 to provide enhanced functionality. In some particularly advantageous embodiments, cartridge information may be obtained by the control system 128 and transmitted to a remote device or devices, such as a smartphone, for displaying various indications, alerts or other information to a user of the appliance 100 based at least in part on the information stored by the cartridge 102 and/or control system 128 of the appliance 100.

For example, FIGS. 8A-8I provide representative screenshots of an application interface 402, which may be provided via a smartphone or other computing device paired with an associated air treatment appliance 100 via wireless communication technology (e.g., Bluetooth, WiFi).

FIG. 8A illustrates a main dashboard screen that provides a user interface for controlling the air treatment appliance 100 through the application. Similar to the controls 107 which may be provided on the appliance 100, the user interface may include controls for powering up and powering down the appliance 100, controls for initiating, pausing and/or stopping a treatment schedule, and controls for modifying the intensity of the treatment, such as, by increasing the amount of aerosolized matter discharged into the space to be treated. The user interface may further include one or more indications pertaining to use and operation of the device, such as, for example, the status of the appliance (e.g., device powered on or device powered off) and the amount of liquid remaining in a cartridge 102 that is installed in the appliance 100. For example, in the context of a cartridge 102 containing a scented liquid compound or liquid fragrance, the user interface may provide a display of the remaining liquid fragrance (e.g., 100% remaining) as depicted in FIG. 8A.

FIG. 8B illustrates a scheduling screen which provides a user interface for creating one or more treatment episodes, which may include, for example, a desired day and time in which air treatment will take place and an intensity level with which the surrounding air will be treated. A plurality of scheduled episodes may be created and saved in memory. The scheduled episodes may be activated and deactivated as desired to manage air treatment activities as desired.

FIG. 8C illustrates a device list screen which provides a user interface for managing a plurality of air treatment appliances that may be managed via the application interface 402. For example, the device list screen may enable a user to select from a list of available appliances 100 for control or management of a particular appliance 100 from the list. A device identifier may be provided for each device, and may be accompanied by an indication of the type of liquid contained in a cartridge 102 associated with the appliance 100.

Figures 8D, 8E, 8F:
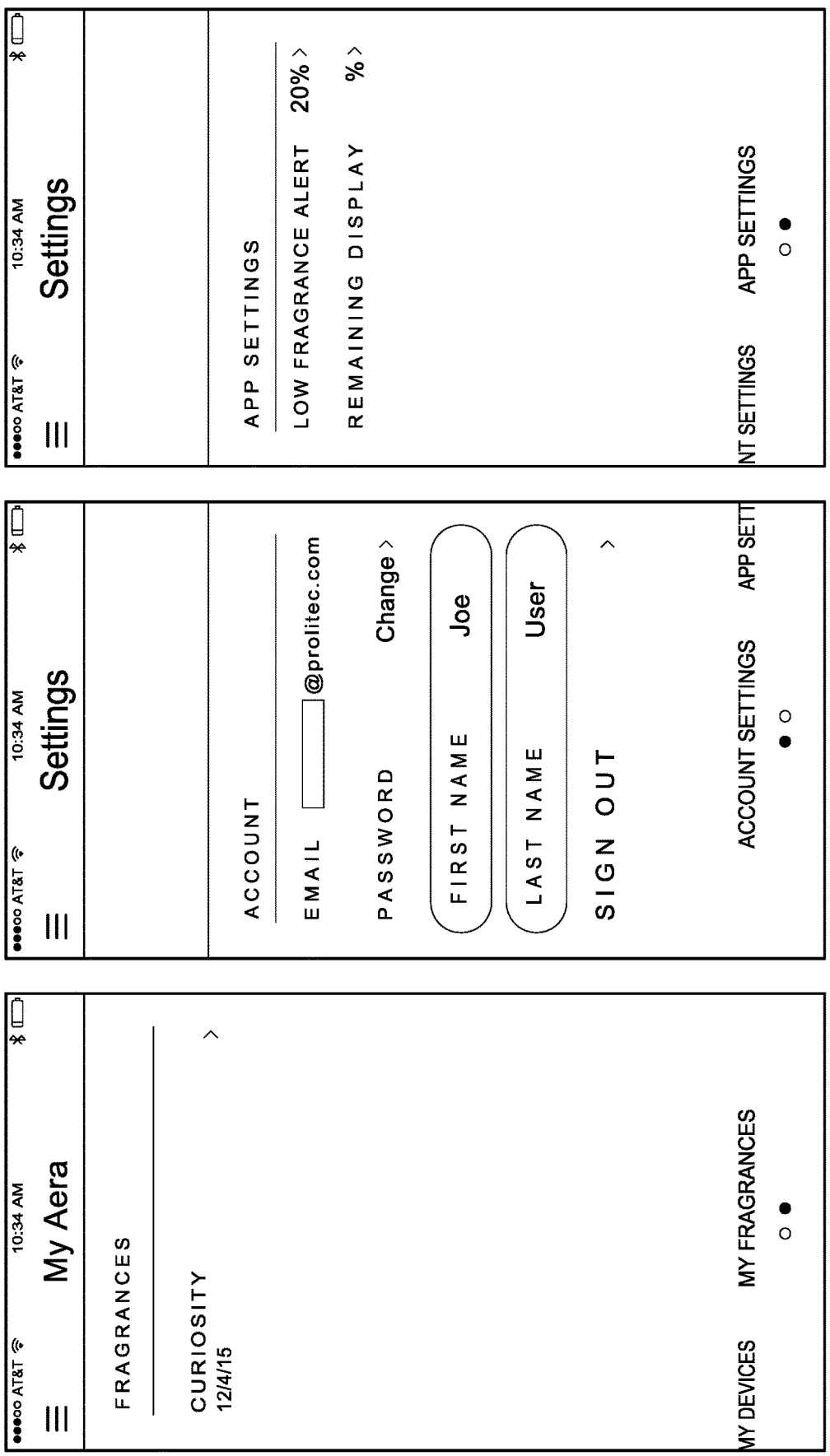

FIG. 8D illustrates a liquid list screen which provides a user interface for displaying information pertaining to the liquid contents of the cartridges 102 loaded in the user's device(s). Such information may include usage history information including the date the cartridge was installed, elapsed run time, intensity level history and/or an amount of remaining liquid in a particular cartridge based on such usage history. The example screenshot of FIG. 8D, for example, indicates a liquid fragrance compound named "curiosity" is available for discharge from a host appliance 100. Operational controls for discharging the liquid fragrance and/or accessing information pertaining to the liquid 120 or host cartridge 102 may be accessed from the list. In addition, functionality may be provided for re-ordering the liquid fragrance and/or setting up automatic replenishment thereof.

FIG. 8E illustrates an account settings screen which provides a user interface for managing account information from which to manage control of the associated liquid diffusion appliance or appliances 100.

FIG. 8F illustrates an app settings screen which provides a user interface for managing various aspects of the application, including, for example, establishing a setting (e.g., 20% of remaining liquid) for generating a low liquid level alert, or establishing a preference for the display type of various data, such as, for example, displaying the remaining liquid in percentage form or alternatively in estimated remaining run time.

Figure 8I:
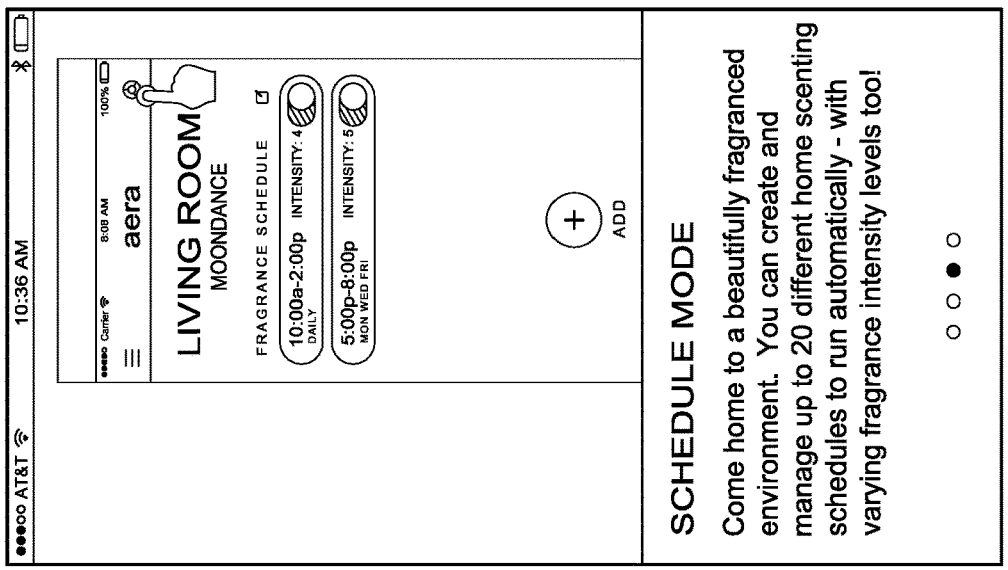
Figure 8H:
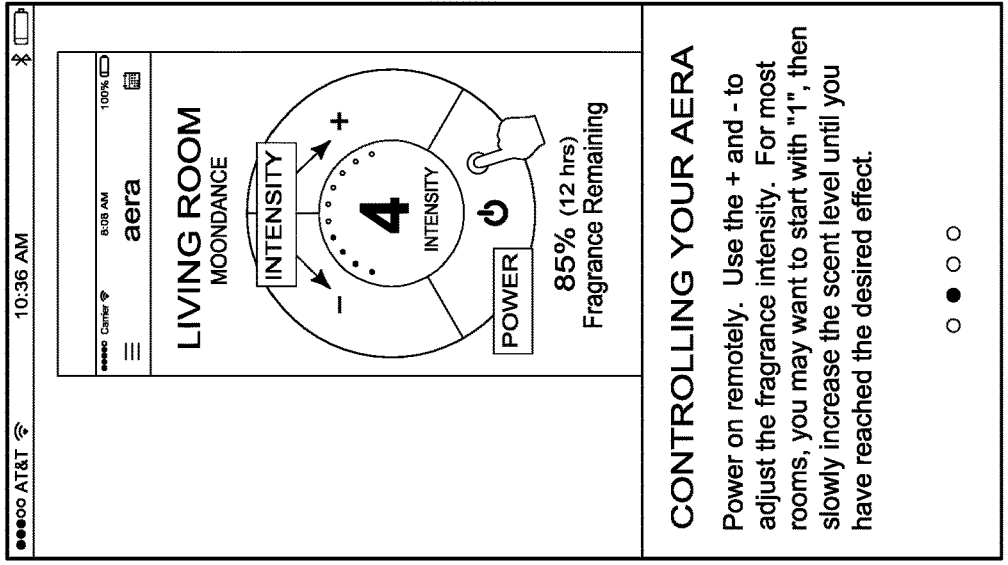
Figure 8G:
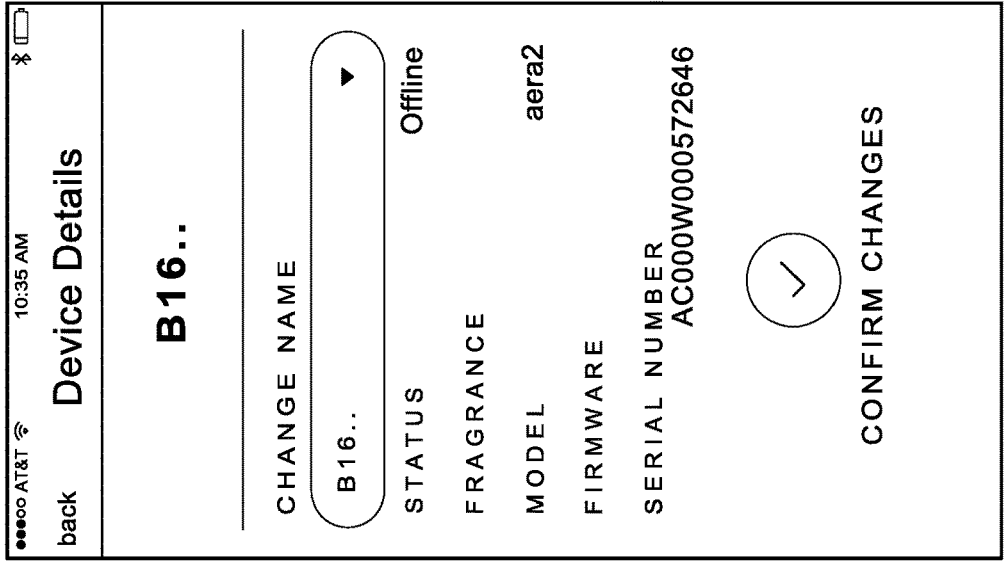

FIG. 8G illustrates an appliance details screen which provides a user interface for accessing information pertaining to one or more user appliances 100. Appliance information may include, for example, device name, device status, type of liquid contained in cartridge 102 loaded in the device, model type, firmware version and update information, and/or appliance serial number or other identifier information. In some instances, the application interface 402 enables a user to customize the name of the user's appliance(s) for ease of recognition, as depicted in FIG. 8G.

FIGS. 8H and 8I illustrate instructional screens which provide instructions and related information to assist in setting up and using one or more air treatment appliances 100 that may be paired with a smartphone or other computing device on which the app may be installed for controlling or otherwise communicating with the appliance(s) 100.

In connection with the various aspects of the user interfaces shown and described with reference to FIGS. 8A through 8I, it is appreciated that a scent delivery system for controllably delivering scented aerosolized matter to an external environment may be provided which includes: a liquid diffusion appliance 100 configured to receive a replaceable cartridge 102 that includes a venturi device 142 for generating the scented aerosolized matter from liquid 120 contained within the replaceable cartridge 102, and configured to move air through the replaceable cartridge 102 to assist in generating the scented aerosolized matter; one or more control circuits; one or more processors; one or more antennas; and at least one memory, the at least one memory including instructions that, upon execution by at least one of the one or more processors via at least one of the one or more control circuits, cause the scent delivery system to provide, via a user interface of a client device (e.g., smartphone) associated with a user of the client device, an indication of an amount of liquid remaining in the replaceable cartridge 102. In some instances, the instructions may further cause the scent delivery system to provide, via the user interface of the client device associated, one or more indications of information related to a power status of the liquid diffusion appliance and/or an intensity of the scented aerosolized matter being generated by the liquid diffusion appliance. In some instances, the instructions may further cause the scent delivery system to provide, via the user interface of the client device, one or more indications of information related to an adjustable delivery schedule of the scented aerosolized matter, including one or more delivery time periods and one or more intensity levels associated with the one or more delivery time periods or portions thereof. In some instances, the instructions may further cause the associated client device or a display of the liquid diffusion appliance to display one or more alerts related to a low amount of liquid remaining in the replaceable cartridge. In some instances, the instructions further cause the associated client device or a display of the liquid diffusion appliance to display one or more indications of information pertaining to characteristics of the replaceable cartridge or liquid contained therein, including an indication of the type of liquid contained in the replaceable cartridge. The liquid diffusion appliance may be one of a plurality of liquid diffusion appliances, and each liquid diffusion appliance may be configured to provide one or more indications of information pertaining to the liquid diffusion appliance and/or a replaceable cartridge received therein to the user interface of the client device. These and other aspects may be provided in connection with a computing device having an installed app for controlling one or more liquid diffusion appliances to which the computing device may be paired.

It may be noted that the air treatment appliances 100, replaceable cartridges 102, and components thereof disclosed herein may include operational control via control system 128 for varying the pressure, flow velocity and/or timing of operation of the onboard air source (e.g., pump 122) to provide air flow through the cartridge 102. In addition to using the control system 128 to alter the amount of liquid diffused or aerosolized by the appliance 100 and the corresponding degree of treatment of a space, the control system 128 may be used to provide other functionality, such as, for example, providing one or more alerts to a user of the appliance 100 related to the state of the fluid level in the cartridge 102 or other indications for facilitating control of the appliance or otherwise enhancing user experience, such as, for example, providing an interface through which to schedule the release of the aerosolized matter from the cartridge 102, as discussed above. Again, this may include, for example, a GUI provided on a smartphone or other computing device that may be paired with the appliance 100 through the use of wireless communication technology, which may allow a user to set the timing and intensity of different air treatment episodes. As such, a user may be able to tailor air treatment activities as desired, such as, to coordinate the release of scented compounds into a room at a time or times when the user is expected to be present or in advance of the expected arrival of one or more occupants.

In connection with the embodiments described herein, it will be also appreciated that various related methods may be provided. For example, one example method implemented by a processor-based electronic liquid diffusion device, such as, for example, the appliance 100 of FIG. 1, may be summarized as including: receiving a signal indicative of a replaceable cartridge 102 being received by the liquid diffusion device 100, the replaceable cartridge 102 containing liquid 120 to be aerosolized; authenticating the replaceable cartridge 102 to ensure compatibility with the liquid diffusion device 100 based on identification data stored by the replaceable cartridge 102; controlling movement of the replaceable cartridge 102 from a cartridge loading position LP to an operational position (not shown) after authenticating the replaceable cartridge 102; and controlling air flow through the replaceable cartridge 102 to discharge aerosolized matter generated from the liquid 120 contained in the authenticated replaceable cartridge 102. The method may further include periodically controlling the replaceable cartridge to move to a home position HP (or weigh position), and collecting data indicative of a level of liquid 120 remaining in the replaceable cartridge 102. The data may then be used to provide fluid level feedback functionality, such as, by providing an indication of fluid level via a client device or the liquid diffusion device 100 itself. For example, the data indicative of the level of fluid remaining in the replaceable cartridge may be transmitted to a client device (e.g., smartphone) for displaying a remaining amount of liquid 120 to a user as the amount decreases from a full amount to an empty amount. In this manner, a user can, among other things, reorder one or more cartridges 102 in response to a low level indication. In addition, in some instances, a user may establish automatic replenishment of cartridges 102 when certain predefined conditions are met (e.g., current cartridge drops to 20% of full capacity).

In some instances, collecting the data indicative of the level of fluid remaining in the replaceable cartridge 102 may include sensing a weight of the replaceable cartridge 102 via a sensor 330 contained in the liquid diffusion device 100. This may include direct or indirect measurement using one or more suitable sensors, such as, for example, a force sensor or optical sensor.

In some instances, authenticating the replaceable cartridge 102 may include receiving cartridge identification data through a connection made between an electrical interface 184 of the replaceable cartridge 102 and a corresponding electrical contact 356 of a lift mechanism 300 used to move the replaceable cartridge 102 between the cartridge loading position LP and the operational position. In this manner, the quality of air treatment can be more accurately controlled by ensuring that only compatible cartridges 102 are used in the liquid diffusion device 100.

Again, although certain specific details are set forth in order to provide a thorough understanding of various disclosed embodiments, one skilled in the relevant art will recognize that embodiments may be practiced without one or more of these specific details. Moreover, aspects and features of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application No. 62/366,987, filed Jul. 26, 2016, are incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A replaceable cartridge for a liquid diffusion device, the replaceable cartridge comprising:

a cartridge housing defining an internal housing cavity partially filled with a liquid to be aerosolized;

a venturi device positioned within the internal housing cavity for generating aerosolized matter from the liquid contained in the internal housing cavity; and wherein the cartridge housing includes a plurality of housing pieces fixedly coupled together to define the internal housing cavity partially filled with the liquid to be aerosolized, wherein the plurality of housing pieces include an internal housing body defining at least a portion of a receptacle for the liquid to be aerosolized, an upper housing cap including an outlet through which the aerosolized matter is discharged during use, and an outer casing surrounding at least a lower portion of the internal housing body, wherein a first coupling arrangement is provided to secure the upper housing cap to the internal housing body and a second coupling arrangement is provided to secure the outer casing to the internal housing body, and wherein the first coupling arrangement includes a coupling protrusion engaged with a coupling cavity, the coupling protrusion provided on one of an outer surface of the internal housing body and an inner surface of the upper housing cap, and the coupling cavity provided on the other one of the outer surface of the internal housing body and the inner surface of the upper housing cap, and wherein the second coupling arrangement includes a second coupling protrusion engaged with a second coupling cavity, the second coupling protrusion provided on one of an outer surface of the internal housing body and an inner surface of the outer casing, and the second coupling cavity provided on the other one of the outer surface of the internal housing body and the inner surface of the outer casing.

2. The replaceable cartridge of claim 1, further comprising:

an integrated circuit coupled to the cartridge housing having memory to store cartridge data associated with the replaceable cartridge.

3. A replaceable cartridge for a liquid diffusion device, the replaceable cartridge comprising:

a cartridge housing defining an internal housing cavity partially filled with a liquid to be aerosolized;

a venturi device positioned within the internal housing cavity for generating aerosolized matter from the liquid contained in the internal housing cavity;

an integrated circuit coupled to the cartridge housing having memory to store cartridge data associated with the replaceable cartridge; and an electrical interface in electrical communication with the integrated circuit to enable retrieval of the cartridge data by an external system contacting the electrical interface, the electrical interface including at least one annular conductor to enable electrical contact with the external system in any rotational orientation about an axis of the replaceable cartridge.

4. The replaceable cartridge of claim 3, wherein the cartridge housing includes a plurality of housing pieces fixedly coupled together to define the internal housing cavity partially filled with the liquid to be aerosolized, and wherein the plurality of housing pieces include an internal housing body defining at least a portion of a receptacle for the liquid to be aerosolized, an upper housing cap including an outlet through which the aerosolized matter is discharged during use, and an outer casing surrounding at least a lower portion of the internal housing body.

5. The replaceable cartridge of claim 4 wherein the internal housing body is transparent or semi-transparent, the outer casing is opaque, and the outer casing includes a window through which a level of the liquid to be aerosolized is viewable through an exposed portion of the internal housing body.

6. The replaceable cartridge of claim 4 wherein the internal housing body defines at least a portion of a gas supply conduit that extends from a bottom end of the replaceable cartridge to the venturi device and through the liquid to be aerosolized.

7. The replaceable cartridge of claim 6, further comprising:

a liquid retention device separate and distinct from the gas supply conduit and insertably received within the gas supply conduit adjacent the venturi device to retain liquid that may pass downward through the venturi device into the gas supply conduit.

8. The replaceable cartridge of claim 7 wherein in the liquid retention device is a liquid retaining plug insertably received within the gas supply conduit.

9. The replaceable cartridge of claim 7 wherein in the liquid retention device is an air permeable plug insertably received within the gas supply conduit.

10. The replaceable cartridge of claim 7 wherein in the liquid retention device is a liquid absorbent plug insertably received within the gas supply conduit.

11. The replaceable cartridge of claim 4, further comprising:

an insert positioned above of the venturi device, the insert including an inlet to receive aerosolized matter generated by the venturi device, an outlet zone from which to discharge the aerosolized matter toward an external environment, and a tortuous passage extending between the inlet and the outlet zone; and a gasket positioned between an upper end of the insert and the upper housing cap, the gasket forming a cover over the tortuous passage extending between the inlet and the outlet zone of the insert.

12. The replaceable cartridge of claim 4 wherein a first coupling arrangement is provided to secure the upper housing cap to the internal housing body and a second coupling arrangement is provided to secure the outer casing to the internal housing body.

13. The replaceable cartridge of claim 12 wherein the first coupling arrangement is configured to prevent non-destructive disassembly of the internal housing body from the upper housing cap, and wherein the second coupling arrangement is configured to enable disassembly of the outer casing from the internal housing body upon overcoming a threshold resistive force.

14. The replaceable cartridge of claim 3 wherein the cartridge housing includes a plurality of housing pieces fixedly coupled together, the plurality of housing pieces including:

an internal body defining the internal housing cavity partially filled with the liquid to be aerosolized;

a cap fixedly coupled to the internal body to enclose the venturi device within a combination of the cap and the internal body; and an outer casing surrounding at least a lower portion of the internal body.

15. The replaceable cartridge of claim 3, further comprising:

a circuit board coupled to the cartridge housing, the circuit board comprising the integrated circuit and the electrical interface.

16. The replaceable cartridge of claim 15 wherein the circuit board is located at a bottom end of the cartridge housing and has an annular shape.

17. The replaceable cartridge of claim 15 wherein the circuit board is located at a bottom end of the cartridge housing and the at least one annular conductor is located at a lower exposed face of the circuit board.

18. The replaceable cartridge of claim 15 wherein a gas supply conduit extends from a bottom end of the replaceable cartridge to the venturi device and through the liquid to be aerosolized, and wherein the circuit board is located at the bottom end of the cartridge housing and surrounds an inlet of the gas supply conduit.

19. The replaceable cartridge of claim 3 wherein the cartridge data includes cartridge identification data, liquid characteristic data, liquid level data and/or cartridge use data.

20. The replaceable cartridge of claim 3 wherein the cartridge housing includes an outlet through which the aerosolized matter is discharged during use, and wherein the integrated circuit is located at a bottom end of the cartridge housing remote from the outlet.

21. A replaceable cartridge for a liquid diffusion device, the replaceable cartridge comprising:

a cartridge housing defining an internal housing cavity partially filled with a liquid to be aerosolized;

a venturi device positioned within the internal housing cavity for generating aerosolized matter from the liquid contained in the internal housing cavity;

a gas supply conduit that extends from a bottom end of the replaceable cartridge to the venturi device and through the liquid to be aerosolized; and a liquid retention device separate and distinct from the gas supply conduit and insertably received within the gas supply conduit adjacent the venturi device to retain liquid that may pass downward through the venturi device into the gas supply conduit.

22. The replaceable cartridge of claim 21 wherein in the liquid retention device is a liquid retaining plug insertably received within the gas supply conduit.

23. The replaceable cartridge of claim 21 wherein in the liquid retention device is an air permeable plug insertably received within the gas supply conduit.

24. The replaceable cartridge of claim 21 wherein in the liquid retention device is a liquid absorbent plug insertably received within the gas supply conduit.

25. The replaceable cartridge of claim 21, further comprising:

an integrated circuit coupled to the cartridge housing having memory to store cartridge data associated with the replaceable cartridge.

* * * * *